(12) United States Patent
Zamir et al.

(10) Patent No.: US 7,235,719 B2
(45) Date of Patent: Jun. 26, 2007

(54) CULTIVATED TOMATO PLANT HAVING INCREASED BRIX VALUE AND METHOD OF PRODUCING SAME

(75) Inventors: Dani Zamir, Gedera (IL); Tzili Pleban, Kiriat Ono (IL); Eyal Fridman, Rehovot (IL)

(73) Assignee: De Ruiter Seeds R&D B.V., Bergschenhoek (NL)

( * ) Notice: Subject to any disclaimer, the term of this patent is extended or adjusted under 35 U.S.C. 154(b) by 299 days.

(21) Appl. No.: 10/302,906

(22) Filed: Nov. 25, 2002

(65) Prior Publication Data

US 2003/0135886 A1 Jul. 17, 2003

Related U.S. Application Data

(63) Continuation-in-part of application No. 09/477,380, filed on Jan. 4, 2000, now abandoned.

(51) Int. Cl.
*A01H 5/00* (2006.01)
*A01H 5/10* (2006.01)
*A01H 1/00* (2006.01)
*A01H 5/08* (2006.01)

(52) U.S. Cl. .................. 800/317.4; 800/260; 800/263; 800/269

(58) Field of Classification Search ................ 800/266, 800/267, 269, 317.4, 263, 260, 278
See application file for complete search history.

(56) References Cited

U.S. PATENT DOCUMENTS 5,523,520 A * 6/1996 Hunsperger et al. ........ 800/260

OTHER PUBLICATIONS

Tanksley et al. Genetics 132: 1141-1160 (1992).*
Rick, CM. Hilgardia 42: 493-510 (1974).*
Eshed et al. Theor Appl Genet 88: 891-897 (1994).*
Eshed et al. Theor Appl Genet 93: 877-886 (1996).*
Eshed et al. Genetics 143: 1807-1817 (1996).*
Kraft et al. Theor Appl Genet 101: 323-326 (2000).*
Azanza et al. Theor. Appl. Genet. 87:965-972 (1994).*
Bernacchi et al. Theor. Appli. Genet. 97:170-180 (1998).*
van Ooijen et al. Theor. Appl. Genet. 89:1007-1013 (1994).*
Kumar, L.S. Biotechnology Advances 17: 143-182, 1999.*
Tanksley et al. Theor. Appl. Genet. 92: 213, 1996.*
Fulton et al. Theor. Appl. Genet. 100: 1025, 2000.*
Frary et al. Theor. Appl. Genet. 108: 485, 2004.*
Fridman et al. Science 305: 1786, 2004.*
Eshed et al. Theor. Appl. Genet. 93: 877-886, 1996.*
King et al. 1997. A Dictionary of Genetics, fifth ed. p. 336.*
Poehlman, J.M. and D.A. Sleper. 1995. Breeding Field Crops. 4th ed. Iowa State University Press, Ames, Iowa, p. 473.*
Herrington et al. HortScience 20(5): 958-959, 1985.*
Fridman et al, "A Recombination Hotspot Delimits a Wild-Species Quantitative Trait Locus for Tomato Sugar Content to 484bp Within an Invertase Gene", *PNAS*, 97(9):4718-4723, 2000.
Eshed et al, "Less-Than-Additive Epistatic Interactions of Quantitative Trait Loci in Tomato", *Genetics*, 143:1807-1817, 1996.
Eshed et al, "An Introgression Line Population of *Lycopersicon pennelli* in the Cultivated Tomato Enables the Identification and Fine Mapping of Yield-Associated QTL", *Genetics*, 141:1147-1162, 1995.
Hamilton, et al, "Construction of Tomato Genomic DNA Libraries in Binary-BAC (BIBAC) Vector", *The Plant Journal*, 18(2):223-229, 1999.
Georgiev, H. "Heterosis in Tomato Breeding", Chap. 8 of Monographs on Theoretical and Applied Genetics vol. 14 Genetic Improvements of Tomato (ed. By Prpf. Kalloo), Springer-Verlag Berlin Heidelberg 1991.
Ori et al, "A Genomic Search for the Gene Conferring Resistance to Fusarium Wilt in Tomato", *Euphytica*, 79:201-204, 1994.
Bernacchi et al, "Advanced Backcross QTL Analysis of Tomato. II. Evaluation of Near-Isogenic Lines Carrying Single-Donor Introgressions for Desirable Wild QTL-Alleles Derived from *Lycopersicon hirsutum* and *L. pimpinellifolium* ", *Theor Appl Genet*, 97:170-180, 1998.
Van Ooijen et al, "An RFLP Linkage Map of *Lycopersicon peruvianum* ", *Theor Appl Genet*, 89:1007-1013, 1994.
Fridman et al, "Two Tightly Linked QTLs Modify Tomato Sugar Content Via Different Physiological Pathways", *Mol Genet Genomics*, 266:821-826, 2002.
Bennett et al, "Exotic Germ Plasm or Engineered Genes", Chap. 8 of *Genetically Modified Foods*, Eds. Engel et al, Symposium of American Chemical Society, Div. Agricultural and Food Chemistry, 1994, pp. 88-99.
Paterson et al, "Mendelian Factors Underlying Quantitative Traits in Tomato: Comparison Across Species, Generations, and Environments", *Genetics*, 127:181-197, 1991 (abstract).

* cited by examiner

*Primary Examiner*—David T. Fox
*Assistant Examiner*—Keith O. Robinson
(74) *Attorney, Agent, or Firm*—Banner & Witcoff, Ltd.

(57) ABSTRACT

A cultivated tomato plant having a genome including an introgression derived from a green-fruited tomato, the green-fruited tomato being characterized by fruits having a brix value above 5 brix units, the introgression including a portion of chromosome 9 of the green-fruited tomato, the portion extending telomerically to a point so as to exclude from the portion an allele of the green-fruited tomato being responsible for an undesired trait selected from the group consisting of higher percent green fruit yield and longer internodes characterizing the green-fruited tomato as is compared to the cultivated tomato plant, the introgression inherently increasing by at least 6% a brix value characterizing fruits of the cultivated tomato plant as is compared to a nearly isogenic tomato plant lacking the introgression.

23 Claims, 18 Drawing Sheets

CULTIVATED TOMATO PLANT HAVING INCREASED BRIX VALUE AND METHOD OF PRODUCING SAME

This is a Continuation-In-Part of U.S. patent application Ser. No. 09/477,380, filed Jan. 4, 2000, now abandoned.

FIELD AND BACKGROUND OF THE INVENTION

The present invention relates to the introgression of a quantitative trait loci (QTL) responsible for high sugar content from green-fruited tomato into cultivated tomato plants. More particularly, the present invention relates to tomato plant lines in which introgression of a green-fruited tomato QTL into a cultivated tomato genetic background resulted in a general cultivated tomato phenotype having fruits characterized by a higher sugar content and brix values.

Ever since the emergence of modern agriculture, cultivated plants have been manipulated in an effort to establish crops with agronomically important traits.

Such traits typically include, plant yield and quality, enhanced growth rates and adaptation to various growth conditions.

Presently a great deal of emphasis is placed on the generation of plants having desired traits via genetic engineering techniques. Over the past decade, advances have been made in developing methods of transferring genes to plant cells (see Potrykus et al., Plant Mol. Bio. Rep. 3:117–128 (1985)). For example, transfer and expression of single genes improving insect and herbicide resistance has reportedly been achieved in plants (Abel et al., Science 232:738–743 (1986); Shah et al., Science 233:478–481 (1986)). While there is excitement over advances in plant genetic engineering, the prospects for the general use of these techniques for plant improvement are tempered by the realization that very few genes corresponding to plant traits of interest have been identified or cloned. Furthermore, agronomically important traits such as, for example, plant yield, height, maturity, and fruit and grain characteristics, are all attractive targets for biotechnological manipulation techniques. However, these traits are often the result of the activity of several genes and as such, the use of direct gene transfer in manipulating these traits, is difficult due to problems in pinpointing and then cloning the individual loci which contribute predominantly to the expression of the trait.

As such, currently practiced approaches for producing plants having agronomically important traits generally rely on conventional plant breeding programs in which plants of a different genotype are genetically crossed in order to produce a hybrid with a recognizable agronomically important trait.

Such an agronomically important trait may be an easily recognizable morphological characteristic such as, for example, fruit size or color, or alternatively traits which are difficult or expensive to evaluate may be selected for by using an indirect selection criteria (Hallaver and Miranda, Quantitative Genetics in Corn Breeding Iowa State University Press 1981). One indirect selection criterion, for example, might be an easily recognized morphological characteristic of the plant which is either genetically linked to the desired trait or perhaps a component of the desired trait, e.g., the association between leaf size and seed size in beans.

Although conventional plant breeding has been used extensively for producing plants having agronomically important traits, such an approach is often difficult to apply to quantitative inherited traits which are determined by the activity of quantitative trait loci (QTL).

Thus, influencing heritability of quantitative inherited traits is difficult, because expression of a number of different gene products generally influences the phenotype. Quantitative traits are characterized by continuous rather than discrete distribution of phenotypic values. There is currently a poor understanding of how single genes influence the expression of complex traits and, in conventional plant breeding programs, selection for inheritance of quantitative traits is difficult due to the unrecognized genetic basis of the trait (Berger, Proceedings of the International Conference on Quantitative Genetics (Pollack et al., Eds., p. 191–204, Iowa St. Press 1977).

Complete linkage maps of DNA markers have facilitated mapping of genes affecting quantitative inherited traits (Paterson et al, Genetics 127: 181–197, 1991 and Tanksley Annu. Rev. Genet. 27:205–233, 1993). Such marker maps must be produced from a suitable mapping population which posses sufficient polymorphism for marker analysis and for quantitative traits. For a self pollinated crop such as for example, tomato, little variation between cultivated varieties is detectable by DNA markers. To overcome this problem, studies of quantitative loci were performed on wide crosses between species or races.

The cultivated tomato (*Lycopersicon esculentum*) is a self-pollinated vegetable crop which is widely cultivated. Tomato's well-endowed genetic resources include 877 monogenic mutations and more than 1000 accessions representing eight wild species. More than 1000 RFLP markers, spanning 1200 centimorgans (cM), have been positioned on the tomato linkage map, providing the basis for resolving quantitative traits into discrete Mendelian factors. The self-pollinated nature of the cultivated tomato enables the construction of populations that segregate for two alleles only at each locus, thereby simplifying analyses of the associations between markers and quantitative traits. Most quantitative trait loci (QTL)-mapping studies in tomato have been conducted on progenies of interspecific crosses, because within *L. esculentum* there is very low DNA-marker and phenotypic variation. Another reason for attempts to map QTL originating from exotic germplasm arise from the fact that the genome of the cultivated tomato, as is the case for many other crop plants, represents only a small fraction of the variation present in the gene pool of the species.

Various tomato plant lines in which introgressions of wild tomato were introduced into a cultivated tomato genetic background were generated in efforts to isolate quantitative trait loci.

One of the major objectives in tomato breeding is to increase the content of total soluble solids (TSS or brix; mainly sugars and acids) of the fruits in order to improve taste and processing qualities. It is known that the TSS content in fruits of wild *Lycopersicon* species can reach up to 15% (15 brix units) of the fresh weight, which is three times higher than cultivated varieties grown under similar conditions. To resolve the genetic basis for this variation, Eshed and Zamir (Genetics 141: 1147–1162, 1995), generated a set of 50 introgression lines from a cross between the green-fruited *L. pennellii* and the cultivated tomato, *L. esculentum*. Each of the lines contained a single RFLP defined *L. pennellii* chromosome segment, and together the lines provide complete coverage of the genome. Using this approach the study performed by Eshed and Zamir demonstrated mapping of 23 QTLs that regulate brix. Although the hybrid plants generated by this study were characterized by a high brix value, phenotypically such plants were further characterized by a small fruit mass, large foliage non-uniform ripening, large internodes and other undesirable characteristics which make such plants unsuitable candidates for commercial applications.

In further studies conducted by Eshed and Zamir (Genetics 143: 1807–1817, 1996) an attempt was made to further isolate the high brix value QTLs. This study uncovered that epistasis, which is a case in which one gene masks or interferes with the phenotypic expression of one or more genes at other loci, plays a key role in QTLs affecting fruit mass and total soluble solids, suggesting that some QTLs that affect these continuous traits in the same direction, interact in a less than additive manner.

Although these studies characterized several QTLs which are thought to be responsible for high brix value, introgression of the most prominent QTL into a cultivated tomato background introduced therein adverse genetic traits, such as high green percentage and long internodes, rendering the resulting tomato plants inapplicable for commercial purposes.

The present invention relates to the dissection of the introgression described by Eshed and Zamir in Genetics 143: 1807–1817, 1996, so at to obtain cultivated tomato plants having fruits characterized by increased brix values, yet are devoid of the adverse genetic traits.

The phenotypic and marker data for all lines have been previously published (Eshed and Zamir 1995), except for IL2-6-1, IL 9-2-5 and IL 12-1-1, which were derived from the fine mapping of QTL of their parental ILs (IL2-6, IL9-2 and IL 12-1; Eshed and Zamir, unpublished results). IL9-2 and IL12-1, with introgressed segments of 37 and 15 cM, respectively, were trimmed to generate IL9-2-5 and IL12-1-1 (9 and 4 cM, respectively). To unify data representation, the deviation of each ILHab from its expected value (interaction effect) is presented in $\Delta\%$ from M82. For example, ILH1-1 increased B by 15% as compared to M82; ILH9-2-5 increased B by 22% as compared to M82. The expected effect for the hybrid between the two homozygous ILs (IL1-1 and IL9-2-5) is a 37% increase in B relative to M82. The observed B for the hybrid heterozygous for the two introgressions was only 26% higher than M82, indicating a significant interaction.

SUMMARY OF THE INVENTION

According to one aspect of the present invention there is provided a cultivated tomato plant having a genome including an introgression derived from a green-fruited tomato, the green-fruited tomato being characterized by fruits having a brix value above 5 brix units, the introgression including a portion of chromosome 9 of the green-fruited tomato, the portion extending telomerically to a point so as to exclude from the portion an allele of the green-fruited tomato being responsible for an undesired trait selected from the group consisting of higher percent green fruit yield and longer internodes characterizing the green-fruited tomato as is compared to the cultivated tomato plant, the introgression inherently increasing by at least 6% a brix value characterizing fruits of the cultivated tomato plant as is compared to a nearly isogenic tomato plant lacking the introgression.

According to another aspect of the present invention there is provided a method of generating a tomato plant having fruits characterized by an increased brix value, the method comprising the step of introgressing to a genome of the tomato plant an introgression derived from a green-fruited tomato, the green-fruited tomato being characterized by fruits having a brix value above 5 brix units, the introgression including a portion of chromosome 9 of the green-fruited tomato, the portion extending telomerically to a point so as to exclude from the portion an allele of the green-fruited tomato being responsible for an undesired trait selected from the group consisting of higher percent green fruit yield and longer internodes characterizing the green-fruited tomato as is compared to the cultivated tomato plant, the introgression inherently increasing by at least 6%, preferably at least 7%, more preferably between at least 7% and 15%, most preferably at least 16–50% or more, a brix value characterizing fruits of the cultivated tomato plant as is compared to a nearly isogenic tomato plant lacking the introgression. As used herein and in the claims section that follows, the phrase "inherently increasing" is indicative of the fact that the introgression carries a brix QTL derived from the green-fruited tomato. As such, an evidence to this inherent property of the introgression may come by an introduction thereof into any cultivated variety, as if further exemplified and described in the Examples section which follows.

According to further features in preferred embodiments of the invention described below, the portion extends telomerically not beyond tomato marker sp9 (SEQ ID NO:1 as a probe and EcoRV as a restriction enzyme), thereby preventing an introduction into the cultivated tomato of the undesired trait.

According to still further features in the described preferred embodiments the fruits of the cultivated tomato plant are characterized by an average brix value above N, whereas N is selected from the group consisting of 5, 6, 7 and 8 brix units.

According to still further features in the described preferred embodiments the fruits of the cultivated tomato plant are characterized by an average fruit mass greater than 30 grams.

According to still further features in the described preferred embodiments a percent green fruit yield of the cultivated tomato plant is below 50%.

According to still further features in the described preferred embodiments internodes of the cultivated tomato plant are shorter than 15 cm.

According to still further features in the described preferred embodiments the cultivated tomato is of a determinant or semideterminant tomato line.

According to still further features in the described preferred embodiments the cultivated tomato is *Lycopersicon esculentum*.

According to still further features in the described preferred embodiments the green-fruited tomato is *Lycopersicon pennellii*.

According to still further features in the described preferred embodiments the cultivated tomato is of an indeterminant tomato line.

According to still further features in the described preferred embodiments the cultivated tomato is selected from a range of genotypes used in the production of commercial tomato varieties.

According to still further features in the described preferred embodiments there is claimed a tomato fruit derived from the tomato plant.

According to still further features in the described preferred embodiments there is claimed a tomato product derived from the tomato fruit.

According to still further features in the described preferred embodiments there is claimed a tomato seed derived from a crossing in which at least one of the parents is the tomato plant.

According to still further features in the described preferred embodiments the tomato seed of claim is a hybrid tomato seed.

According to yet another aspect of the present invention there is provided a method of generating a tomato plant having fruits characterized by an increased brix value, the method comprising the steps of: (a) crossing a first cultivated tomato with a tomato line containing a green-fruited tomato introgression and having a fruit brix value higher than that of said first cultivated tomato, so as to generate a first hybrid tomato characterized by a fruit brix value higher than that of the cultivated tomato; (b) crossing the first hybrid tomato or offspring thereof with a second cultivated tomato being characterized by a phenotype different than the first cultivated tomato; and (c) isolating offspring resulting from step (b) characterized by a phenotype of the second cultivated tomato yet with fruits having a higher brix value than that of fruits of the second cultivated tomato.

According to still further features in the described preferred embodiments the method further comprises the step of: (d) selfing the offspring resultant from step (c) so as to establish a tomato line characterized by a phenotype of the second cultivated tomato yet with fruits having the higher brix value than that of fruits of the second cultivated tomato.

The present invention successfully addresses the shortcomings of the presently known configurations by providing a cultivated tomato plant including a high brix QTL of a green-fruited tomato introgressed thereto. The cultivated tomato plant according to the present invention is characterized by fruits having a brix value higher than that of a nearly isogenic non-introgressed tomato plant while at the same time having a general phenotype of said nearly isogenic non-introgressed cultivated tomato plant.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show the various aspects of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
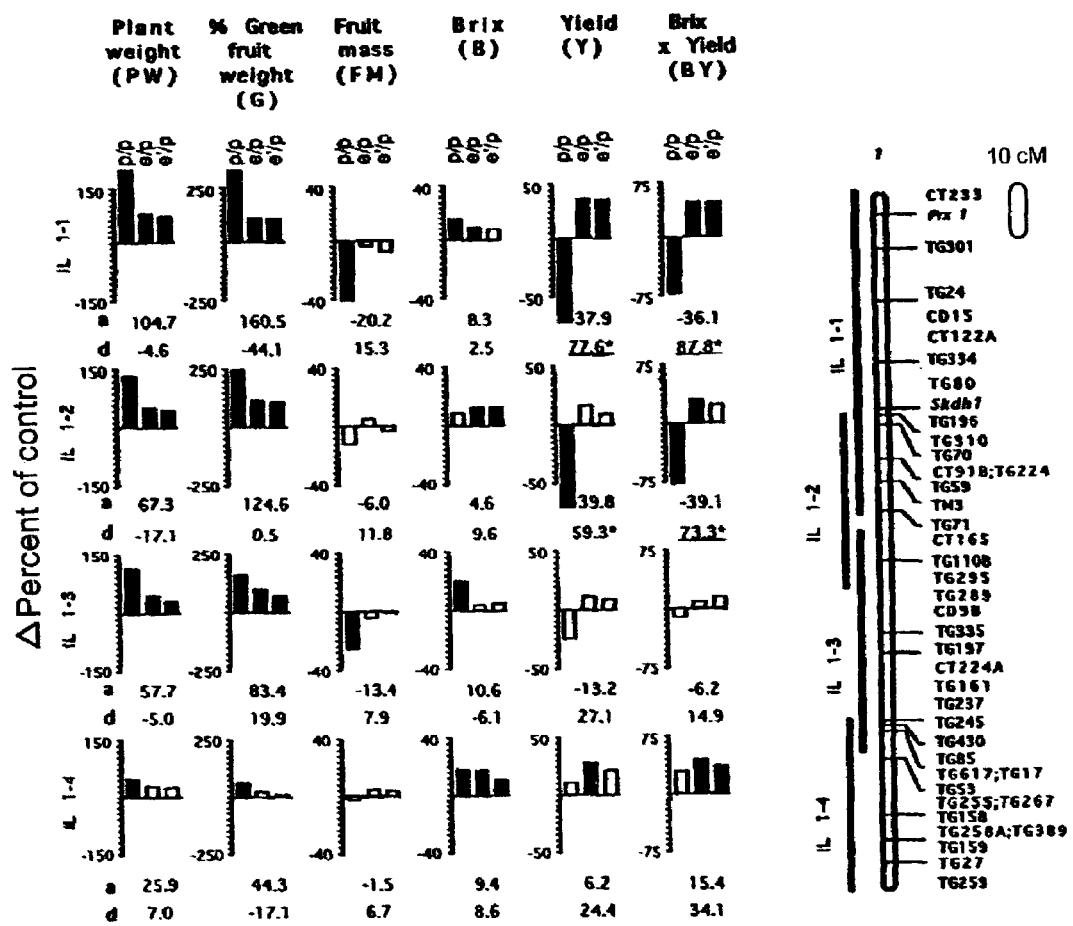
FIGS. 1a–i depict the chromosomal locations, sizes and identities of the 50 L. pennellii introgression lines (ILs) on chromosomes 1–12. The genetic map was constructed on the basis of 119 BC1 plants as described by Eshed and Zamir (1995). Mapped markers which are associated with the chromosome of a plant line, and markers not assayed on the BC1 map are placed according to their approximate positions based on Tanksley et al. Each line was probed with all the markers, and lines showing wild-species alleles are marked with bars to the left of the chromosome. e—L. esculentum, p—L. pennellii (Prior art).
Figure 1B:
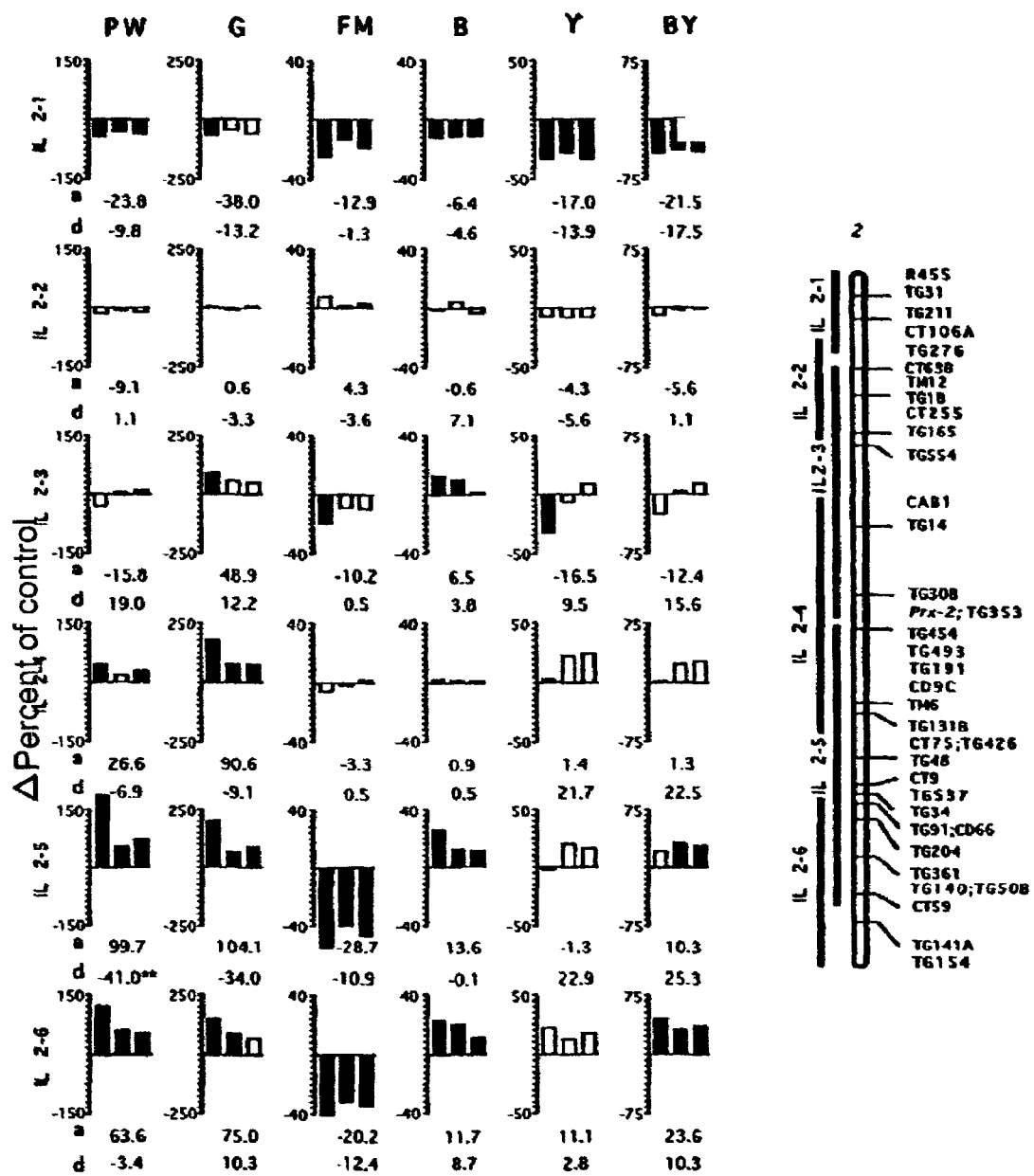
Figure 1C:
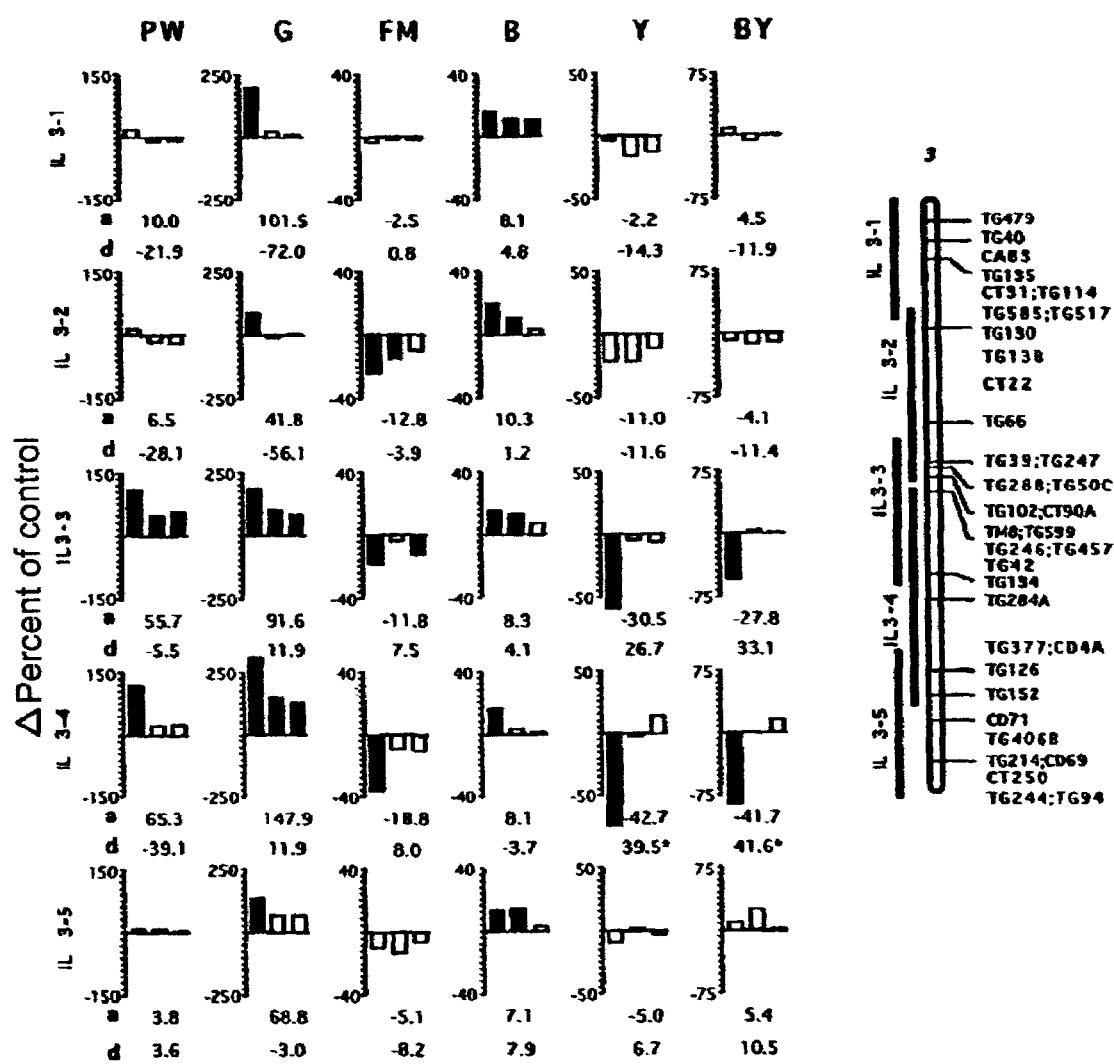
Figure 1D:
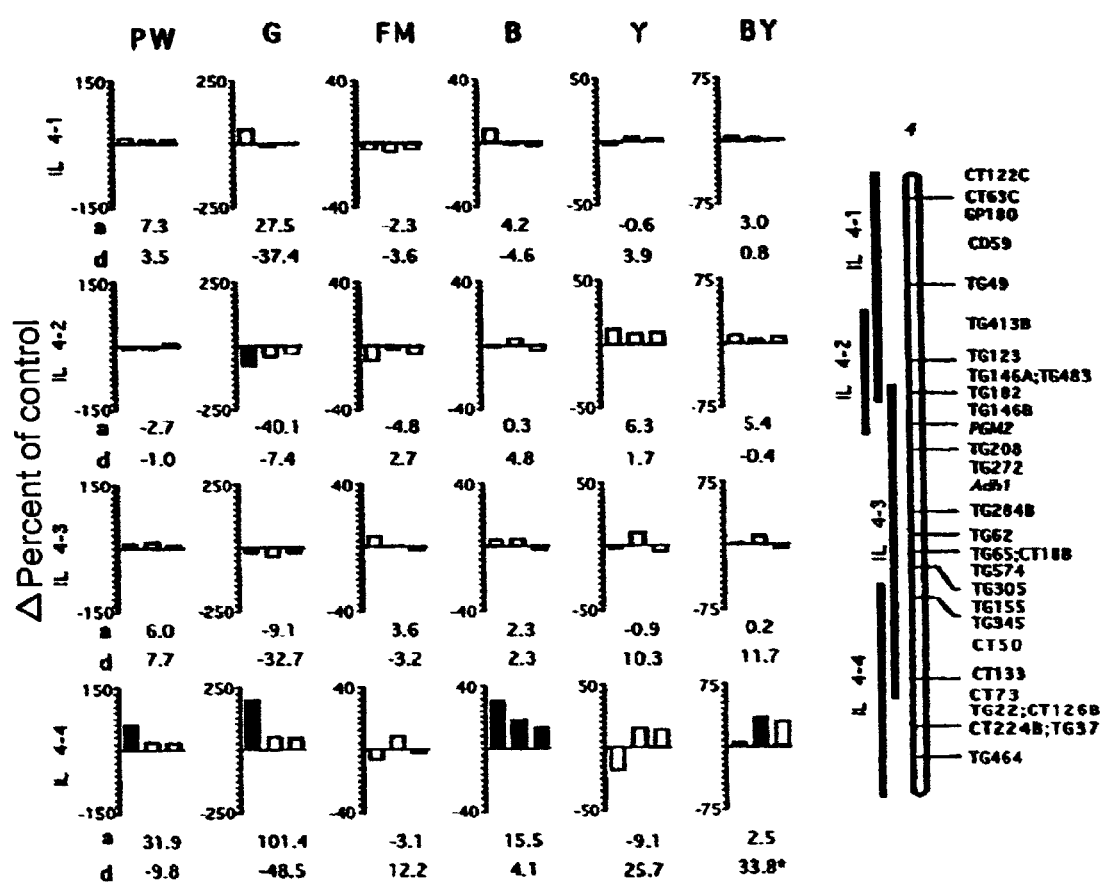
Figure 1E:
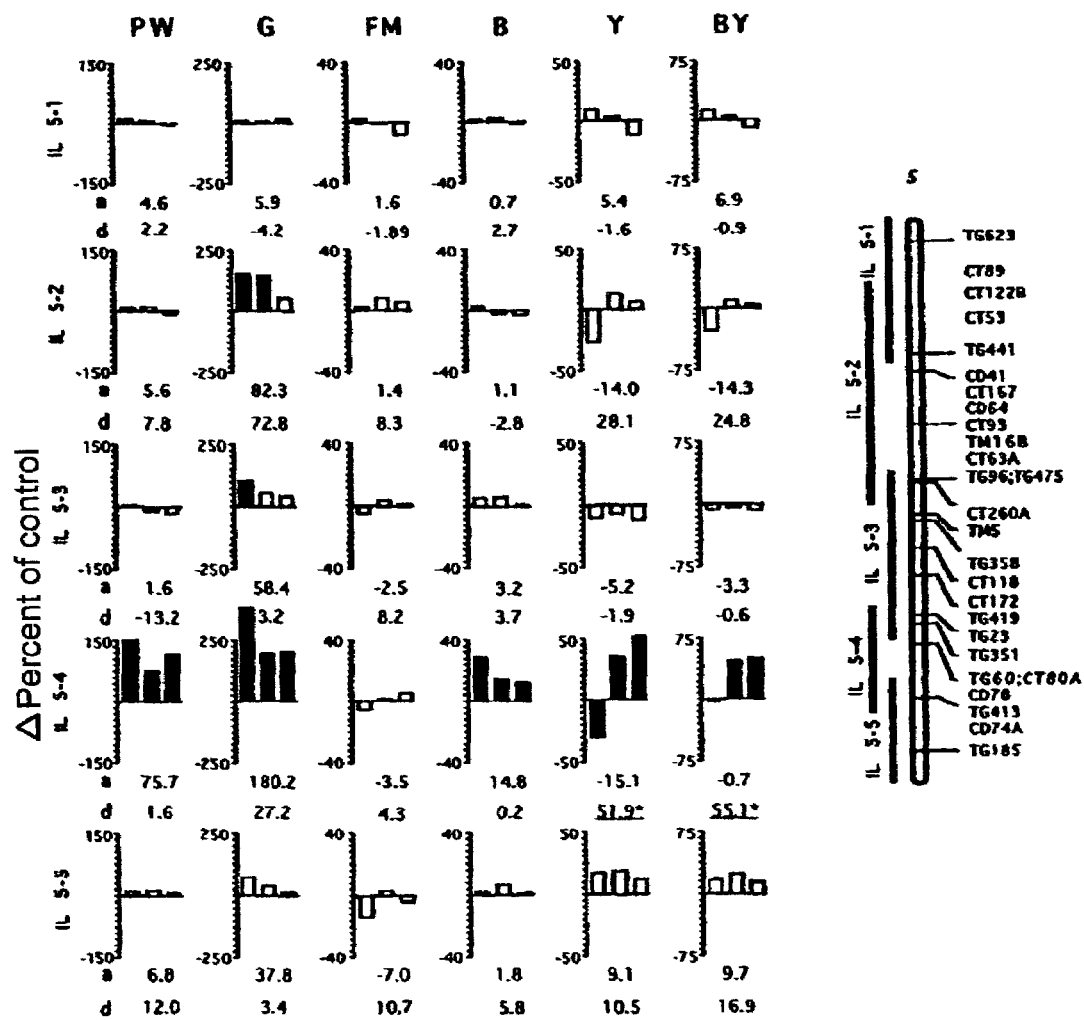
Figure 1F:
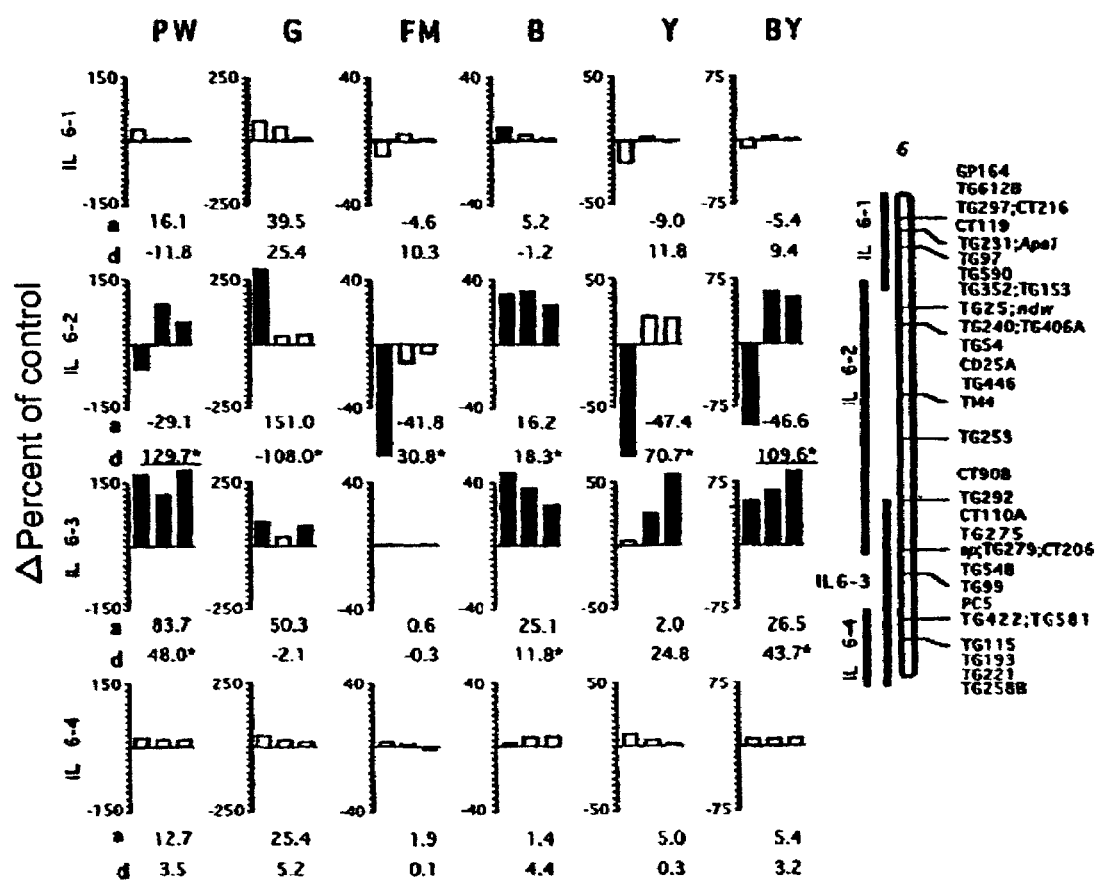
Figure 1G:
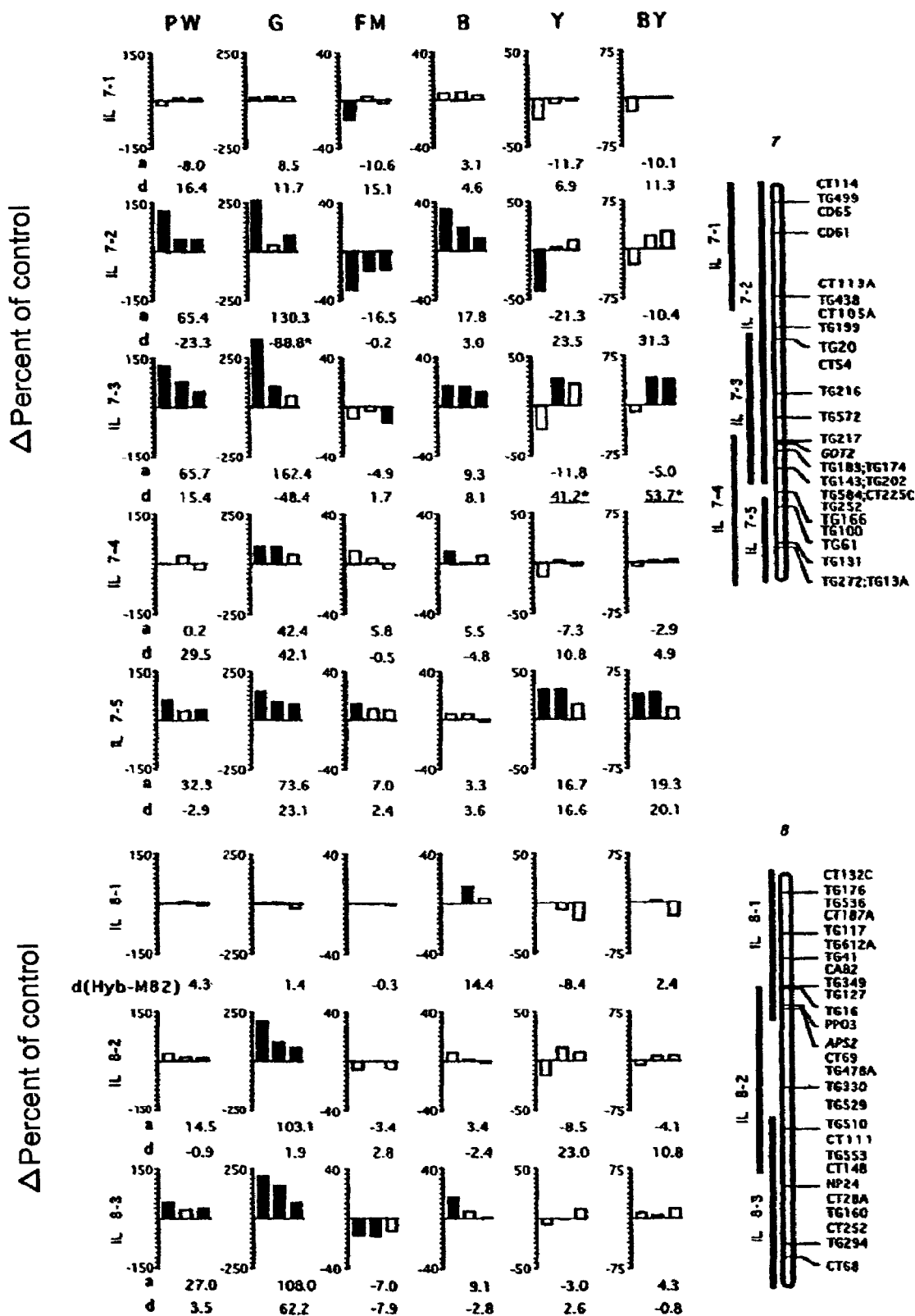
Figure 1H:
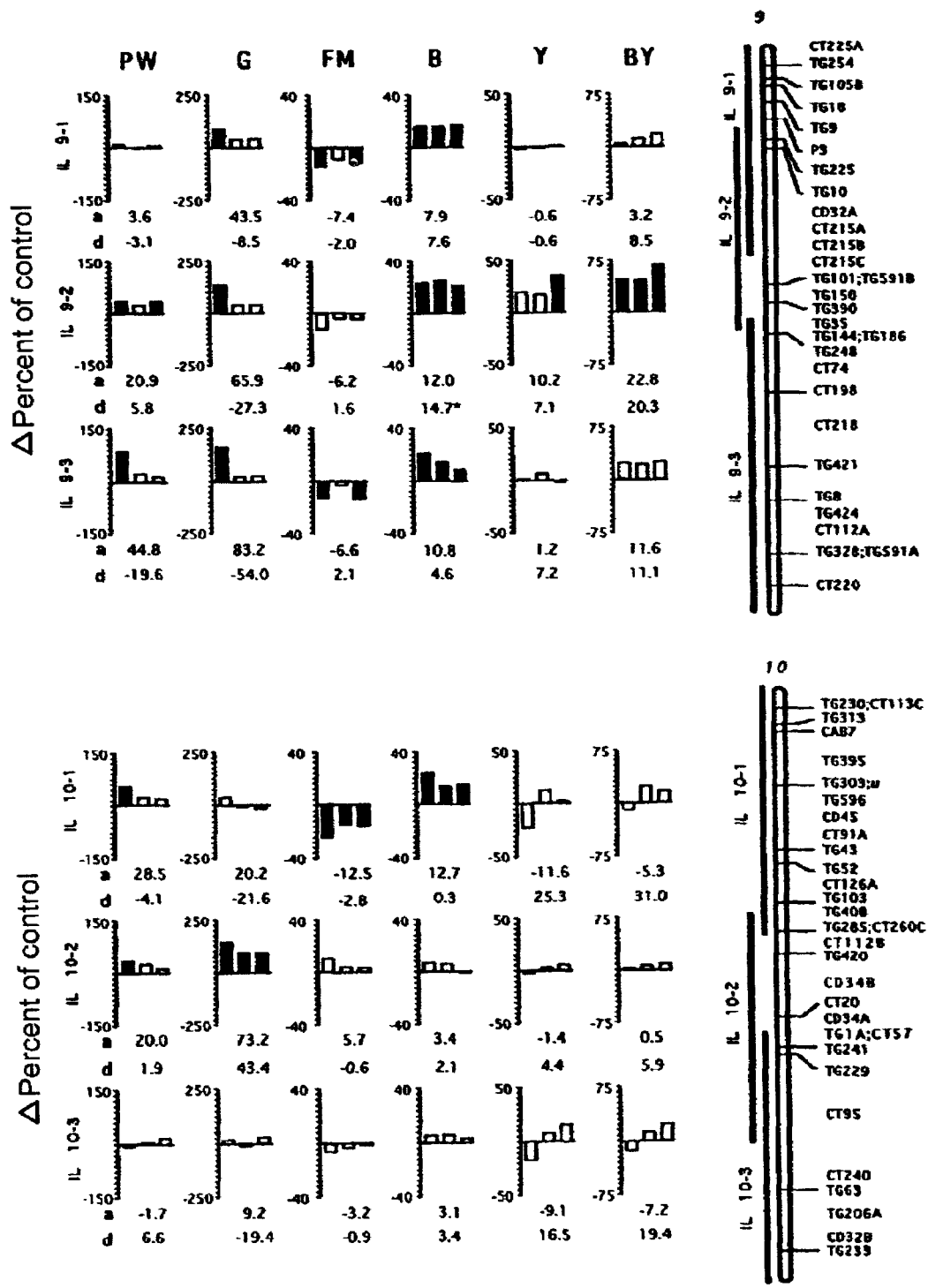
Figure 1I:
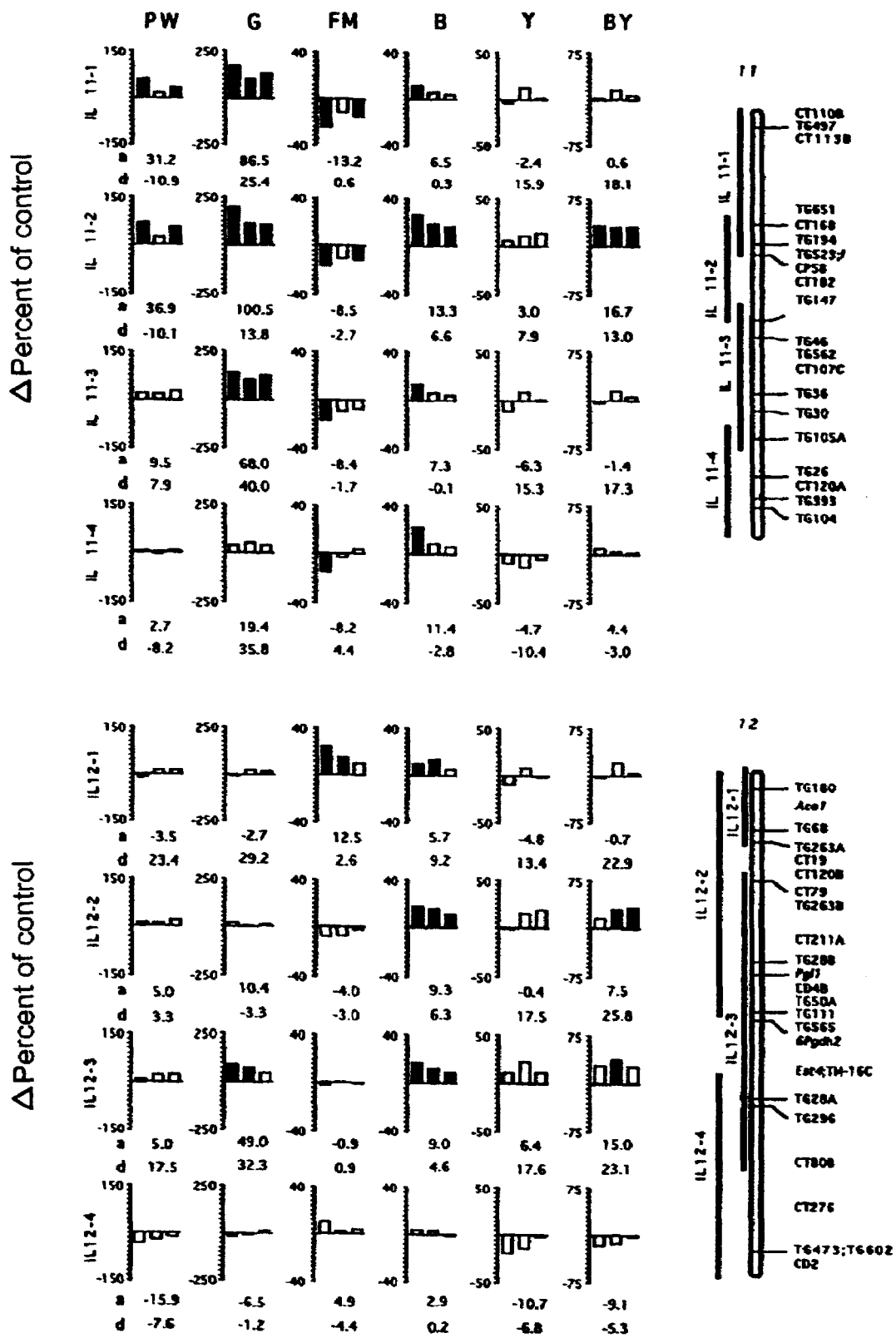

The present invention is of a chromosome 9 region of a green-fruited tomato, which region, when introgressed into a cultivated tomato genetic background increases the brix value of the fruits produced thereby.

Specifically, the present invention is of a centromeric portion of an introgression from chromosome 9 of green-fruited tomato, which was previously described by Eshed and Zamir in Genetics 143: 1807–1817, 1996. This novel chromosome 9 fragment which spans from a region between tomato markers SP 9 and GP 263 to a region between tomato markers p14.1 and CP 44 is capable of, when introgressed into the genetic background of a cultivated tomato, increasing the brix value of fruits produced thereby, while at the same time maintaining the desired phenotypic traits of the cultivated tomato, such as shorter internodes and lower percent green fruit yield as is compared to a green-fruited tomato.

The principles and operation of the present invention may be better understood with reference to the accompanying descriptions.

Before explaining at least one embodiment of the invention in detail, it is to be understood that the invention is not limited in its application to the details set forth in the following description. The invention is capable of other embodiments or of being practiced or carried out in various ways. Also, it is to be understood that the phraseology and terminology employed herein is for the purpose of description and should not be regarded as limiting.

Brix-associated quantitative trait loci (QTLs) have been thoroughly described in the prior art.

As further described in Examples 1 and 2 of the Examples section, Eshed and Zamir (1995 and 1996, ibid) have characterized 23 QTLs which are also associated with an increase in a brix value of tomato fruits. These QTLs were mapped to various chromosomes and chromosomal locations of the tomato genome.

Although prior art studies performed by Eshed and Zamir, clearly associated the marker defined QTLs with high brix values, the isolation of the brix trait from other linked and otherwise undesirable traits was not achieved by these studies. As a result, plants produced by introgressions described in these studies, in addition to including a desired high brix value trait, included undesirable traits inherited from the green-fruited tomato. Such traits included long internodes and a high percent green fruit yield and as such, these plants were unsuitable for commercial purposes.

Initially, IL9-2-5 was described as a line that contains a 9 cM introgression of the wild species *Lycopersicon pennellii* in the background of the cultivated tomato *L. esculentum* var M82 [Eshed, Y. & Zamir, D. *Genetics* 143, 1807–1817 (1996)]. Two flanking markers, CT283 and TG10 (FIG. 10*b*), defined the introgressed segment, according to the high-density molecular map of the tomato [Tanksley, S. D. et al. *Genetics* 132, 1141–1160. (1992)].

However, early mapping experiments that were conducted using segregating populations for the chromosome 9 introgression revealed some inconsistency with the tomato RFLP map that was based on a small F2 population (67 plants).

For this reason, the present inventors re-maped the existing RFLP markers and redefined the IL9-2-5 introgression line based on the new local map generated. Since the two RFLP markers that defined the introgression showed a complete co-segregation in the later populations, additional markers were required in order to outline the introgression with at least two flanking markers. Several approaches were conducted in attempt to identify additional markers that map to the IL9-2-5 introgression:

(i) Since the tomato and potato genomes are nearly collinear [Tanksley, S. D. et al. *Genetics* 132, 1141–1160. (1992); and Chen, X., Salamini, F. & Gebhardt, C. *Theoretical and Applied Genetics* 102, 284–295 (2001)]. Some of the potato RFLP markers that were mapped in the collinear genomic region of potato chromosome 9 were analyzed in order to determine if they map to IL9-2-5. This survey included ten candidate markers and revealed two markers, GP263 and GP272. GP272 was found to co-segregate with TG225 (data not shown) and GP263 was mapped within the introgression (see FIGS. 10*a–b*).

(ii) Mapping of new genes and random markers on the chromosome 9 recombinant population. This survey included the mapping of a member of the Self-pruning (Sp; sp9) [Pnueli, L. et al. *Development* 125, 1979–1989 (1998)] gene family that was found to reside between GP263 and CT283. Acquiring this gene as an RFLP marker included screening a tomato BAC genomic library with the Arabidopsis orthologue and isolation of the corresponding gene in tomato. An additional marker that was mapped to the centromeric part of the introgression, and hence was used with TG225 to define the IL9-2-5 introgression, is p14.1 (see FIGS. 10*a–b*).

It is important to note, that based on the map constructed by the inventors while reducing the present invention to practice, any attempt to recombine the IL9-2-5 using the previously known markers, TG10 and CT283, would have failed since these two markers flank only a small portion of the introgression (the telomeric part). Furthermore, the QTL that increases the brix value, without affecting the internodes of the plant, resides on the far side of these two markers, to the centromeric side of the introgression (see FIG. 10*b*).

Thus, through laborious experimentation, the present inventors have dissected the QTL responsible for an advantageous trait of green-fruited tomato, i.e., high brix value, from at least two other QTLs responsible for adverse traits, i.e., long internodes and high percent green fruit yield (non-uniform ripening) to thereby identify an introgression which enables generation of tomato lines which are particularly suitable for commercial applications.

As used herein the phrase "cultivated tomato plant" refers to a commercially grown tomato plant of an indeterminant or a determinant line, which is generally defined by ripened fruits of at least 30 and typically between 50 and 250 grams in mass, for determinant lines—a percentage of green fruit yield less than 50% (in mass), typically less than 30%, internodes of less than 15 cm, typically less than 10 cm in length, and ripened fruits characterized by a red color and a fruit brix value of 3—6 brix units when grown in a green house under sweet water irrigation. An example of a cultivated tomato plant is *Lycopersicon esculentum* either of a determinant line (i.e., including a self pruning allele designated Sp⁻) or an indeterminant line (Sp⁺). In addition, a cultivated tomato plant according to the present invention may include any genomic alteration introduced via plant breeding or molecular techniques, but which still retain the general cultivated tomato phenotype.

As used herein the phrase "green-fruited tomato" refers to a wild tomato species which is not commercially cultivated. Such a species, which is, for example, represented by *Lycopersicon pennellii* is characterized by small fruits of no more than 10 grams, typically 3 grams in mass and of green color, 100 percent green fruit yield, internodes of more than 15 cm in length and a fruit brix value of 10–15 brix units.

Thus, according to one aspect of the present invention, there is provided, a cultivated tomato plant having a genome including an introgression derived from a green-fruited tomato.

The introgression according to the present invention includes a portion of chromosome 9 of the green-fruited tomato, which extends telomerically so as to exclude an allele of said green-fruited tomato being responsible for an undesired trait selected from the group consisting of higher percent green fruit yield and longer internodes characterizing the green-fruited tomato as is compared to the cultivated tomato plant. The introgression according to the present invention increases by at least 6% and preferably by 6–50% or more a brix value characterizing fruits of the cultivated tomato plant as is compared to a nearly isogenic tomato plant lacking the introgression. As such, the introgression according to the present invention does not include any undesirable trait(s) such as a higher percent green fruit yield and longer internodes which are associated with chromosomal regions which are positioned telomerically to the brix QTL.

According to a preferred embodiment of the present invention, this portion extends telomerically not beyond tomato marker sp9, thereby preventing an introduction into the cultivated tomato of the undesired trait(s). Most preferably, the introgression spans from a region between tomato markers SP 9 and GP 263 to a region between tomato markers p14.1 and CP 44. For further detail of this portion of chromosome 9 please refer to FIG. 10b.

Figure 8A:
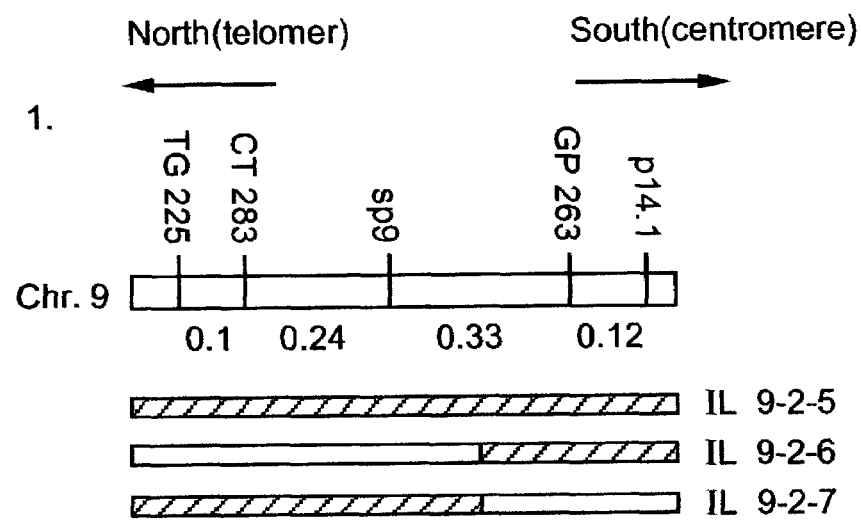
FIG. 8a depicts a genetic map of the IL9-2-5 introgression. The genetic distance in centimorgans (cM) is indicated between each pair of markers and is based on the F2 population. The genotype of IL9-2-5, IL9-2-6 and IL9-2-7 is represented by a hatched bar (L. pennellii) and an empty bar (*L. esculentum*). The border between the two bars is determined arbitrary between the two flanking markers.
Figure 10B:
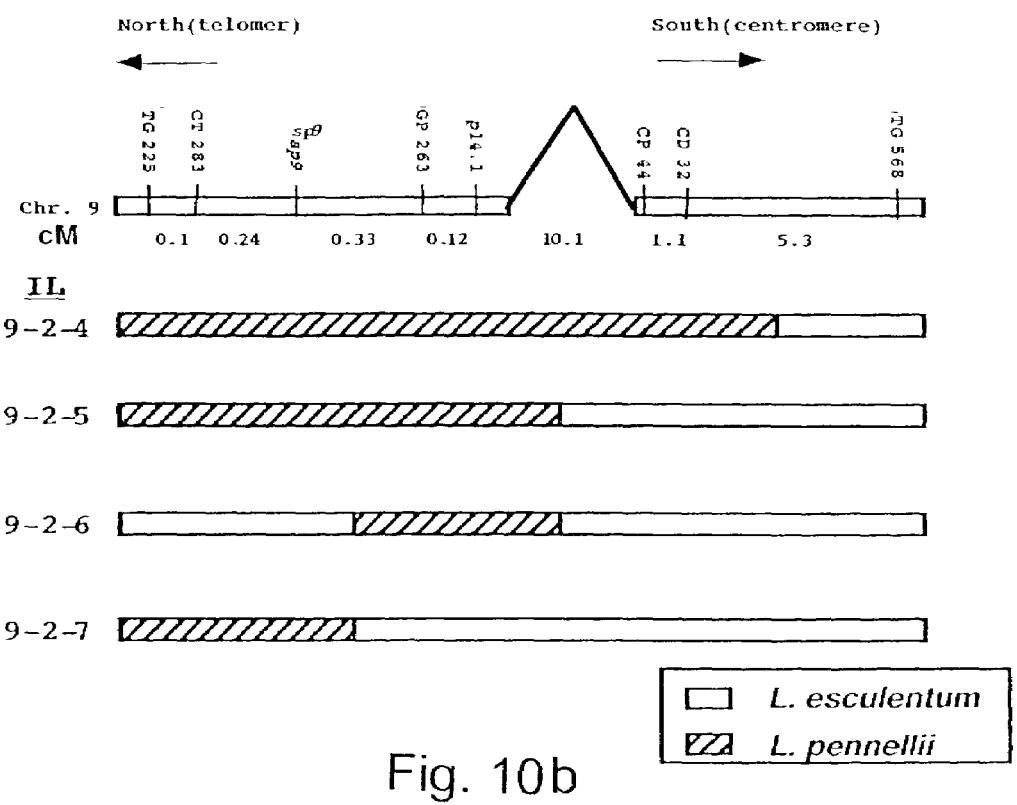

As such, the introgression segment of the present invention, includes the brix QTL but lacks alleles associated with undesirable traits of the green-fruited tomato. The position of the brix introgression on chromosome 9 is illustrated in FIGS. 8a and 10b (denoted as IL9-2-6 therein) and is discussed in detail in Example 3 of the Examples section that follows.

As a result of this introgression, a cultivated tomato progeny either of an f1 generation or any subsequent generation and which include this introgression found either in a heterozygotic state or preferably in a homozygotic state, produces fruit which are characterized by an increased brix value as is compared to a nearly isogenic cultivated tomato plant lacking the introgression.

According to a preferred embodiment of the present invention this increase is by at least 6%, preferably at least 10%, more preferably at least 15%, most preferably at least 20–50% as is compared to a nearly isogenic cultivated tomato plant lacking this introgression and which is grown under identical conditions.

Thus, the introgressed cultivated tomato plant of the present invention and any progeny thereof resultant from crossing the cultivated tomato with unrelated tomato species, with nearly isogenic species, or from self crossing, produce fruits which are characterized by a brix value of at least 4 brix units, at least 5 brix units, preferably at least 6 brix units, more preferably at least 7 brix units, most preferably at least 8 brix units or more when grown in a green house with sweet water irrigation.

In addition to producing fruits with a high brix value, these introgressed tomato plants are further characterized by several traits.

(i) An average fruit mass which is similar to that of a cultivated tomato, and is greater than 30 grams, preferably greater than 50 grams, more preferably greater than 75 grams, most preferably greater than 100 grams. In comparison the average fruit mass of a green-fruited tomato is between 2 to 10 grams, typically about 3 grams.

(ii) A percent green fruit yield of below 50%, preferably below 45%, more preferably below 40%, most preferably below 35%.

(iii) Internodes preferably shorter than 15 cm, more preferably shorter than 14 cm, most preferably shorter than 10 cm. In comparison the internodes in a green-fruited tomato are generally longer than 15 cm.

It will be appreciated that in addition to these traits, the cultivated tomato according to the present invention may further be characterized by, for example, simultaneous ripening of fruit, a high fruit yield, and any other desirable traits which may be determined by the genetic background into which the brix chromosomal segment of the present invention in introgressed.

It will be appreciated that this genetic background may be of any cultivated tomato species or cultivar either genetically modified or not. Examples of suitable tomato plants include a range of genotypes used in the production of commercial tomato varieties, which can be used for processing into tomato paste, dice and whole peel production, fresh market determinate tomatoes for open field production and semideterminate and indeterminate varieties for staked cultivation in the open field or protected nets and for glasshouse.

Thus, according to the present invention there is provided cultivated tomato plants producing fruits and seeds, such as, for example, hybrid seeds, of commercial value, which plants are generated according to the teachings of the present invention by introgressing a chromosomal region associated with a high brix value in green-fruited tomato, into a genetic background of a cultivated tomato.

As with the characterization of other non-brix QTLs documented in the prior art, the isolation of the brix QTL of the present invention from linked undesired traits can be effected by performing numerous introgressions into a single genetic background. However, while reducing the present invention to practice it was discovered that introgressing the chromosomal portion from already introgressed hybrids, which include residual undesired traits, into a second and different genetic background greatly facilitates the isolation and characterization of the chromosomal fragment harboring the brix QTL.

Thus, according to another aspect of the present invention, there is provided a method of generating a tomato plant having fruits characterized by an increased brix value.

In a first step of the method according to this aspect of the present invention, a first cultivated tomato is crossed with a tomato line containing a green-fruited tomato introgression and having a fruit brix value higher than that of the first cultivated tomato. The progeny resultant from this cross which is characterized by a fruit brix value higher than that of the cultivated tomato is isolated. In a second step, the first hybrid tomato or offspring thereof are crossed with a second cultivated tomato which is characterized by a phenotype different than the first cultivated tomato. In a final step of the method according to this aspect of the present invention, the offspring resulting from the previous step, which are characterized by a phenotype of the second cultivated tomato, yet produce fruits having a higher brix value than that of fruits of the second cultivated tomato, are isolated.

The resultant offspring can then be grown in the field or selfed to establish a line of cultivated tomato characterized by fruit having a high brix value and a general cultivated tomato phenotype.

Offspring resultant from the second hybrid cross or progeny of a self crossing thereof, can also be used as a parental line in for example, hybrid crossing, such that cultivated tomato plants which are characterized by fruits having a high brix value, a general cultivated tomato phenotype (as described above) and any other trait which may be inherited from a second parent of the hybrid cross can be produced.

Thus, the present invention provides the identification of a chromosome 9 region which is responsible for a high brix value of green-fruited tomato fruits. The study performed as part of the present invention and which is described in detail in Examples 3 and 4 of the Examples section enabled the identification and association of tomato chromosomal markers with the brix chromosomal portion.

The brix associated chromosomal region was characterized as a result of numerous hybrid crosses in which green-fruited tomato chromosomal fragments were introgressed into a cultivated tomato genetic background. Associating a phenotype resultant from these crosses with chromosomal markers enabled the characterization of the brix QTL region in a portion of chromosome 9.

As a result of this study, a novel cultivated tomato plant was generated, which is characterized by a phenotype similar to that of a nearly isogenic cultivated tomato lacking the green-fruited tomato introgression, and by fruits having a brix value higher than that of the isogenic cultivated tomato. As is further detailed in Examples 3 and 4 of the examples section the brix chromosomal region was introgressed to both a determinant and an indeterminant tomato plant lines, thus generating both determinant and indeterminant tomato plants which produce fruits characterized by a brix value higher than that of non introgressed isogenic cultivated tomato plants.

It will be appreciated that such cultivated tomato plants, and the seeds thereof are of immense value to commercial agriculture, since a crop yield resultant therefrom will be similar in quantity to that of presently grown cultivated tomato plants, while being far superior in quality when compared thereto.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include plant breeding and genetic analysis techniques. Such techniques are thoroughly described in the literature. See, for example, See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); "Genome Analysis: A Laboratory Manual Series", Vols. 1–4, Cold Spring Harbor Laboratory Press, New York (1998); "An introduction to genetic analysis" third edition, Suzuki et al., 1986; and "Molecular Dissection of Complex Traits, Paterson A H 1998, all of which are incorporated by reference as if fully set forth herein. Other general references are provided throughout this document. The procedures therein are believed to be well known in the art and are provided for the convenience of the reader. All the information contained therein is incorporated herein by reference.

Example 1

In previously published results (Eshed and Zamir, 1995, ibid) an *L. pennellii* introgression line (IL) population was designed in order to generate QTL-NILs. This IL population consisted of 50 lines, each containing a single homozygous restriction fragment length polymorphism (RFLP)-defined wild-species chromosome segment. Together these lines provided complete coverage of the tomato genome and a set of nearly isogenic lines (NILs) to their recurrent parent, the processing-tomato cultivar M82 (Rick et al., TGRC stock lists, *Rep. Tom. Genet. Coop.*, 45, 53, 1995) (FIG. 1). The genetic assumption underlying the identification of QTL using the NILs was that any phenotypic difference between an IL and its nearly isogenic control plant is due to a QTL that resides on the chromosome segment introgressed from *L. pennellii*. The minimum number of $p<0.05$-significant QTL affecting a trait in the ILs was calculated on the basis of the following assumptions: (i) each IL affecting a quantitative trait carries only a single QTL; and (ii) two overlapping introgressions with a significant effect on a trait (in the same direction relative to the control) carry the same QTL.

Therefore, in the ILs, the maximum number of detectable QTLs is approximately 30. Despite this limitation, twice as many QTLs responsible for fruit mass (FM) were identified as compared to the previous populations (see Table 1 below). The sensitivity of the ILs in identifying QTLs was even more pronounced for brix (B), where two to six times as many QTLs were identified as compared to the other populations.

TABLE 1

The number of significant effects (p < 0.05) of wild species QTLs on FM and B

| Species | population structure | population size | No. of FM-QTLs | No. of B-QTLs | Reference |
|---|---|---|---|---|---|
| L. chmielewskii | BC1 | 237 | 6 | 4 | Tanksley et al. Genetics, 232, 1141, 1992 |
| L. cheesmanii | F2 | 350 | 7 | 4 | Paterson et al Genetics, 127, 181, 1991 |
| L. pimpinellifolium | BC1 | 257 | 7 | 3 | Grandillo et al Theor. Appl. Genet., 90, 225, 1996 |
| L. cheesmanii | R1 | 97 (6 reps.) | 12 | 14 | Goldman et al Theor. Appl. Genet., 90, 925, 1995 |
| L. pennellii | IL | 50 (6 reps.) | 18 | 23 | Eshed and Zamir 1995, ibid |

Using the *L. pennellii* ILs, QTLs were mapped to various chromosome segments originating from the wild species. However the effects associated with an introgressed segment could be due to the existence of one or more loci.

A 60-cM segment on the long arm of chromosome 2 was responsible for a 60% reduction in FM (in homozygotes) relative to the control, M82. This chromosomal region apparently harbors QTLs responsible for FM, which are common to a number of wild tomato species (Alpert et al. Theor. Appl. Genet., 91, 994, 1995).

Fine-mapping analysis of recombinant lines for that region identified three linked loci with a similar effect on FM; two of which were placed on a 3 cM interval. Finer mapping may reveal additional FM QTL in these regions.

Quantitative effects which appear to be associated with a single locus were inferred from cases of rare transgressive segregation. Using the ILs, 18 QTLs responsible for FM were identified but in only two cases (IL7-5 and IL12-1-1 with introgression sizes of 15 and 4 cM, respectively) alleles of the small-fruited wild species were associated with larger fruits. These effects were consistent in trials conducted in different years and genetic constitutions (Eshed and Zamir, 1996, ibid).

Several features of the IL population contributed to its efficiency in detecting QTLs, even in cases when only a few replicates of each genotype were evaluated.

(i) The lines contained single RFLP-defined introgressions, some of which produce effects of relatively large magnitude in which most of the phenotypic variation between the NILs is associated with the introgressed segment.

(ii) The permanent nature of the lines enabled testing of the introgression effects in different years. The results obtained showed high reproducibility of the effects of the QTL which were mapped to the different introgressed chromosome segments.

(iii) Elimination of the "overshadowing effect" of major QTLs enabled to detect minor QTLs (a major QTL contributes to large phenotypic variation, thereby masking the effects of other QTLs segregating in the same population)

(iv) Elimination of epistatic interactions between unlinked QTLs.

(v) The simple statistical procedure relied on comparison with a common control and is therefore less affected by experimental error.

Gene Actions Revealed by QTL Studies

A gene action of the QTL detected was determined using the IL population described above by comparing the homozygous ILs to hybrids of the ILs with the recurrent parent.

The FM and brix qualities were determined by QTLs which were intermediates between additivity and dominance. This mode of inheritance is in agreement with results obtained by analysis of an F2 generation (Paterson Genetics, 127, 181, 1991). In contrast, fruit yield (Y) was strongly associated with overdominance, whereby some of the heterozygous ILs had higher values relative to their corresponding homozygous parents.

Detailed mapping analysis of a chromosome 1 introgression which showed overdominance for Y suggested the existence of two cis loci with opposing effects. This result was therefore consistent with the pseudo-overdominance model for heterosis (Crow *Heterosis*, Gowen, J. W., Eds., Iowa State College Press, Ames, Iowa, 1952). However for the other heterotic introgressions, including dw-1, the issue of the mode of gene action for heterosis is still unresolved. It is interesting to note that the wild species used for the tomato mapping studies were highly inferior to the cultivated variety with respect to Y, yet chromosome segments from these species contribute to the increased Y of commercially grown varieties. This transgressive segregation is frequent for Y and for seedling morphological traits, whereas for FM and brix, transgression was rare (DeVicente et al Genetics, 134, 585, 1993).

Reproducibility of the Effects of an Identified QTL

Mendelian factors underlying quantitative traits in an interspecific tomato cross were compared in F2 and F3 generations of the same population (Paterson Genetics, 127, 181, 1991). Of 11 FM QTL identified in both generations in a trial conducted in California, six were significant both in F2 and F3. Of the five B QTLs, two were significant in both generations. Differences between generations can result from interactions with the environment and/or may indicate that the resolution power of such populations is limited to QTLs with large effects. In contrast, of 33 yield-associated QTLs identified in a two-year trial of selected ILs, 28 were significant in both experiments (Eshed and Zamir 1996, ibid).

Association Between QTL-NILs and the Introgressed Segment

The use of the L. pennellii ILs to identify QTLs is based on RFLP results which indicated that each line contains a single wild-species introgression. However, some of the lines may include small unidentified introgressions, and these segments may be responsible for the observed phenotypic effects. To test whether the difference between the IL and its nearly isogenic control lies solely in the introgressed segment, a simple experiment was performed using eight selected ILs. An F2 resulting from a cross between each IL and M82 was subjected to RFLP analysis, and plants homozygous for the cultivated-tomato chromosome segment were compared quantitatively to M82. In no case were any differences detected, indicating that the observed phenotypic differences (which were verified using the plants carrying the L. pennellii introgressions) are due to the mapped chromosome to segment.

The ten homozygous ILs were crossed in a half diallele mode and the phenotypic values of the 45 double heterozygotes were compared to the respective single heterozygous ILs and M82. The results which were previously reported by Eshed and Zamir (1996, ibid) indicate that QTL epistasis is prevalent and is generally less than additive.

Figure 2:
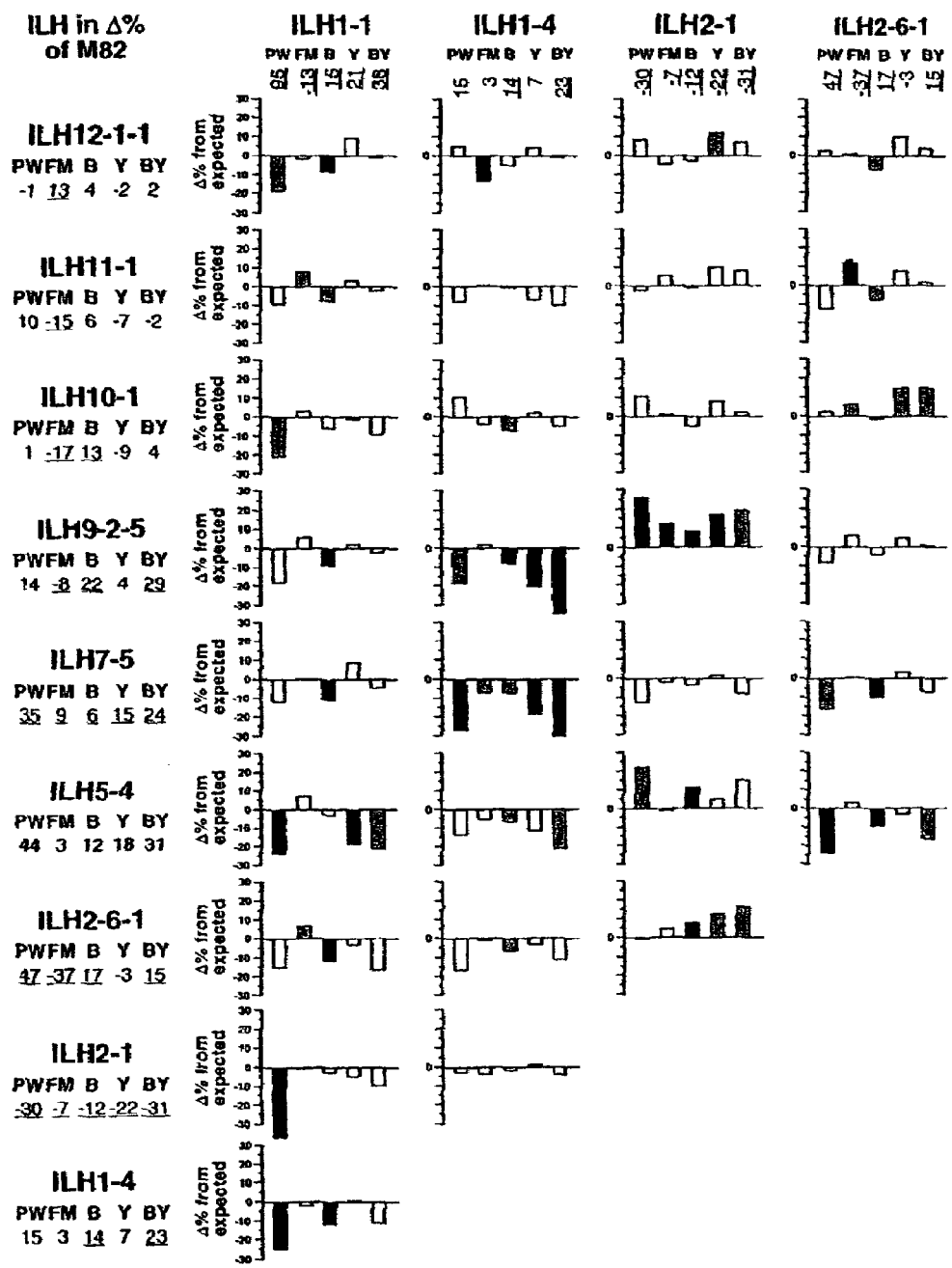
FIG. 2 depicts the digenic interactions between unlinked QTLs. The values on the left and at the top of the Figures are the difference (in %) of each IL hybrid (ILH) from M82 according to Table 2 below. Values in bold are significant at $p<0.05$ (Dunnet's t test). Each histogram represents the difference (in %) of the hybrid heterozygous for the two introgression from the sum of the effect of the two individual ILHs for all traits measured (PW—plant weight, FM—fruit mass, B—brix, Y—total fruit yield, BY—the product of B and Y). Bars in white show no significant interaction and bars in light gray, gray and black indicate significant interactions of $p<0.05$, $p<0.01$ and $p<0.001$, respectively (prior art).

Phenotype of the Selected Single Introgression ILHs:

In the complete IL population composed of 50 introgression line hybrids (ILHs) which was analyzed for five yield-associated traits, 81 of the 250 ILH×trait combinations (32%) were significantly different from the isogenic controls ($p<0.05$). For the subset of the 10 ILHs selected for the interaction study, 30 of the 50 combinations (60%) differed significantly from the control (FIG. 2). This comparison indicates that the 10 ILHs were enriched for QTLs affecting the measured traits.

In this previously reported study, of the 10 ILHs (using the same experimental error), 28 of the 30 significant effects were consistent between the two experiments (Table 2 below; Y for ILH1-4 and BY for ILH2-6-1 were not significantly different from the control).

TABLE 2

Mean phenotypic values of M82 and the IL hybrids heterozygous for single introgressions

| Genotype | Introgressed region 'a' | Number of replicates | plant weight (kg) | fruit mass (g) | brix (0) | Yield (kg) | brix x yield (g) |
|---|---|---|---|---|---|---|---|
| M82 | none | 79 | 1.82 ± 0.44 | 56.1 ± 4.9 | 4.54 ± 0.40 | 9.18 ± 1.54 | 417 ± 82 |
| ILH1-1[b] | 1(CT233-TG7l; 58 cM) | 26 | 3.56 ± 0.84* | 48.6 ± 6.5* | 5.23 ± 0.48* | 11.15 ± 2.34* | 580± 114* |
| ILH1-4 | 1(TG245-TG259; 35 cM) | 23 | 2.10 ± 0.44 | 58.1 ± 5.4 | 5.16 ± 0.39* | 9.84 ± 1.60 | 507± 83 |
| ILH2-1 | 2(R45S-TG276; 16 cM) | 26 | 1.27 ± 0.32* | 52.4 ± 5.4* | 4.01 ± 0.33* | 7.19 ± 1.64* | 289 ± 72* |
| ILH2-6-1[c] | 2(TG91-CT59: 14 cM | 26 | 2.68 ± 0.46* | 35.2 ± 4.5* | 5.30 ± 0.44* | 8.95 ± 1.81 | 474 ± 99 |
| ILH5-4 | 5(TG351-TG413; 16 cM) | 25 | 2.62 ± 0.59* | 57.9 ± 7.1 | 5.07 ± 0.31* | 10.85 ± 2.34* | 551 ± 127* |
| ILH7-5 | 7(TG61-TG131A; 15 cM) | 26 | 2.46 ± 0.46* | 61.5 ± 6.3* | 4.83 ± 0.33* | 10.52 ± 1.45* | 509 ± 87* |
| ILH9-2-5[c] | 9(CT283A-TG10;9 cM) | 25 | 2.09 ± 0.47 | 51.7 ± 6.3* | 5.52 ± 0.26* | 9.58 ± 1.92 | 532 ± 122* |
| ILH10-1 | 10(TG230-TG285; 37 cM) | 24 | 1.84 ± 0.33 | 46.5 ± 5.5* | 5.11 ± 0.31* | 8.38 ± 1.60 | 428 ± 81 |
| ILH11-1 | 11(TG497-TG523; 27 cM) | 26 | 2.06 ± 0.47 | 47.5 ± 3.6* | 4.79 ± 0.41 | 8.50 ± 1.65 | 406 ± 73 |
| 1LH12-1-1[c] | 12(TG180-ACO-1; 4 cM) | 27 | 1.81 ± 0.32 | 63.3 ± 5.4* | 4.70 ± 0.37 | 8.96 ± 1.21 | 422 ± 69 |

Mean phenotypic values and standard deviations of M82 and the ILH that participated in the diallele crosses. All means were compared to M82 and the ones marked with *are significantly different (Dunnet's t-test, $p < 0.05$). Underlined mean values indicate a significant interaction with year (1993 vs., 1995; $0.01<p < 0.05$).
'a' The introgressed regions in the ILHs is indicated by chromosome number, the markers flanking the introgression and its size in cM according to Tanskley et al. (1992) Genetics 132: 1141–1160.
[b]ILH Hybrid of ILs crossed with M82.
[c]Interaction with year was based on unpublished results from a 1994 trial.

Example 2

Epistatic Interactions

The study described in Example 1 (Eshed and Zamir, 1995, ibid) served as a basis for testing epistatic interactions between QTLs. Thus, 10 ILs were selected, some of which include QTLs that affect the measured traits in the heterozygous condition in various directions relative to the control the results obtained were reported.

The effects of ILH7-5 on PW, FM and brix were found to be significant as compared to other previously reported studies. this significance was probably due to the larger number of replicants tested (25 as compared to 6 in previous studies). Significant ILH by year interactions ($p<0.05$) were detected for four of the 50 comparisons (Table 2). These four comparisons were not significantly different from the control in either of the years. These results indicate a high overall reproducibility of the experimental system in different years of growth.

Interactions Between Unlinked Introgressions:

The null hypothesis for the interaction analysis was complete additivity of the effects of the single introgression ILHs. Any significant deviation from complete additivity was considered as epistasis (FIG. 3).

For example, ILH1-1 increased PW by 95% compared to M82; ILH12-1-1 reduced PW by 1% compared to M82. The expected phenotype for the hybrid between the two homozygous ILs (IL1-1 and IL12-1-1) is a 94% increase in PW relative to M82. The observed PW for the hybrid heterozygous for the two introgressions was 76% higher than M82, indicating a significant interaction (p<0.05).

Figure 3:
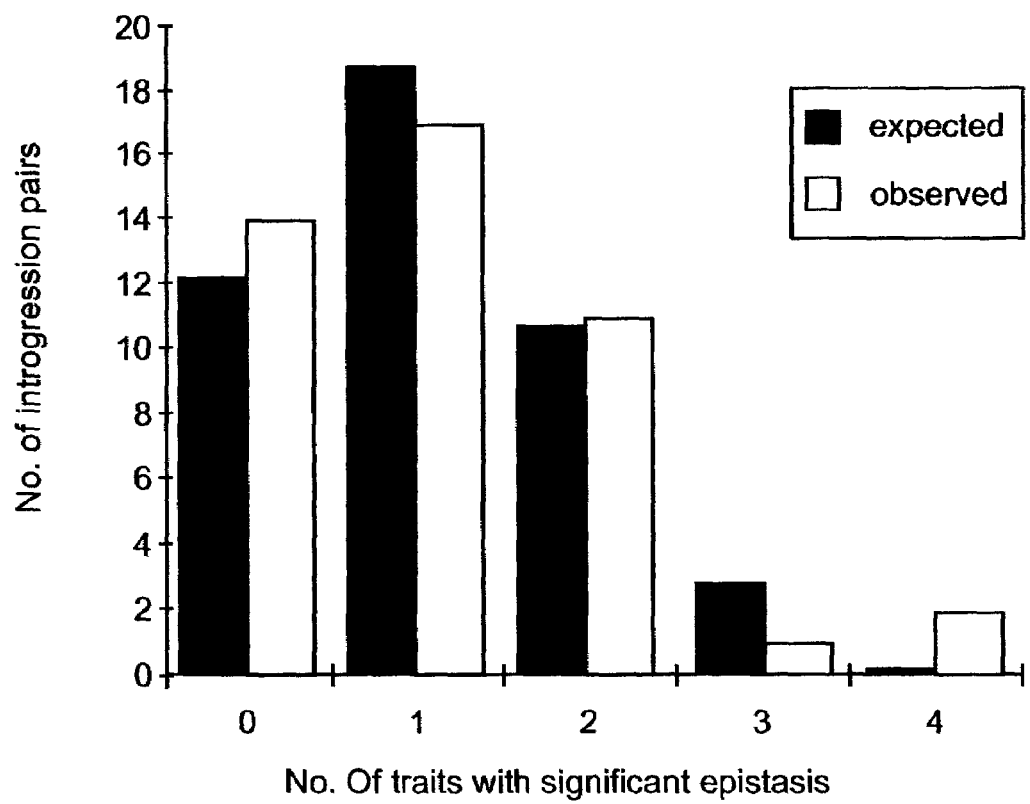
FIG. 3 depicts the distribution of the observed and expected numbers of pairs of introgressions showing simultaneous significant epistasis ($p<0.05$) for the traits: plant weight (PW), fruit mass (FM), brix (B) and yield (Y). The expected values were calculated on the basis of complete independence between traits and a mean epistatic rate of 0.28 for each trait (prior art).

Of the 225 possible interactions (45 hybrids×five traits) 59, 28 and 12 were significant at the p<0.05, p<0.01 and p<0.001 level respectively (FIG. 3). These values are much higher than that expected by chance alone.

To further characterize the nature of the interactions, the double-heterozygous combinations were divided into four groups based on the performance of the single ILHs (Table 3 below)

TABLE 3

Frequency of significant interactions (p < 0.05) between unlinked L. pennellii introgressions

| Interacting QTL types[a] | Plant weight | Fruit mass | brix | Total fruit yield | brixx yield | Sum |
|---|---|---|---|---|---|---|
| Sig-Sig (same direction) | 3[b]/6[c] | 8/16 | 12/21 | 1/3 | 5/15 | 29/61 |
| Sig-Sig (opposite direction) | 2/4 | 1/12 | 3/7 | 0/3 | 1/6 | 7/32 |
| Sig-NonSig | 5/25 | 2/16 | 4/16 | 5/24 | 2/21 | 18/102 |
| NonSig-NonSig | 1/10 | 0/1 | 0/1 | 3/15 | 1/3 | 5/30 |
| Sum | 11/45 | 11/45 | 19/45 | 9/45 | 9/45 | 59/225 |

[a]QTLs were classified according to the significance and the direction of their effects relative to M82.
[b]Number of significant interactions.
[c]Number of tested combinations of two L. pennellii introgressions.

As is shown by Table 3, of 61 tested introgressions between significant QTLs (same direction), 29 (48%) were significant (p<0.05) indicating that the interactions between two significant QTLs of *L. pennellii* affect a trait in the same direction.

Among 32 introgressions between significant (opposite) QTLs, seven (22%) significant interactions were detected indicating that the interaction between two significant QTLs of *L. pennellii* affect the trait in opposite directions. Six of these interactions involved crosses with IL2-1 for PW, B and BY. The IL2-1 line carries the pleiotropic QTL which affected all of these traits. The seventh interaction in this group involved that of IL12-1-1 with IL-10-1 for FM, where IL12-1-1 showed marked transgressive segregation for this trait (Table 2).

Among 102 introgressions between significant and non-significant QTLs 18 (18%) interactions were significant.

Among the 30 introgressions between non-significant QTLs, five (17%) significant interactions were found. Overall, 26% (59/225) of the various *L. pennellii* introgressions showed significant interactions and the proportion of epistatic effects was highest for significant same direction QTLs.

Figure 4:
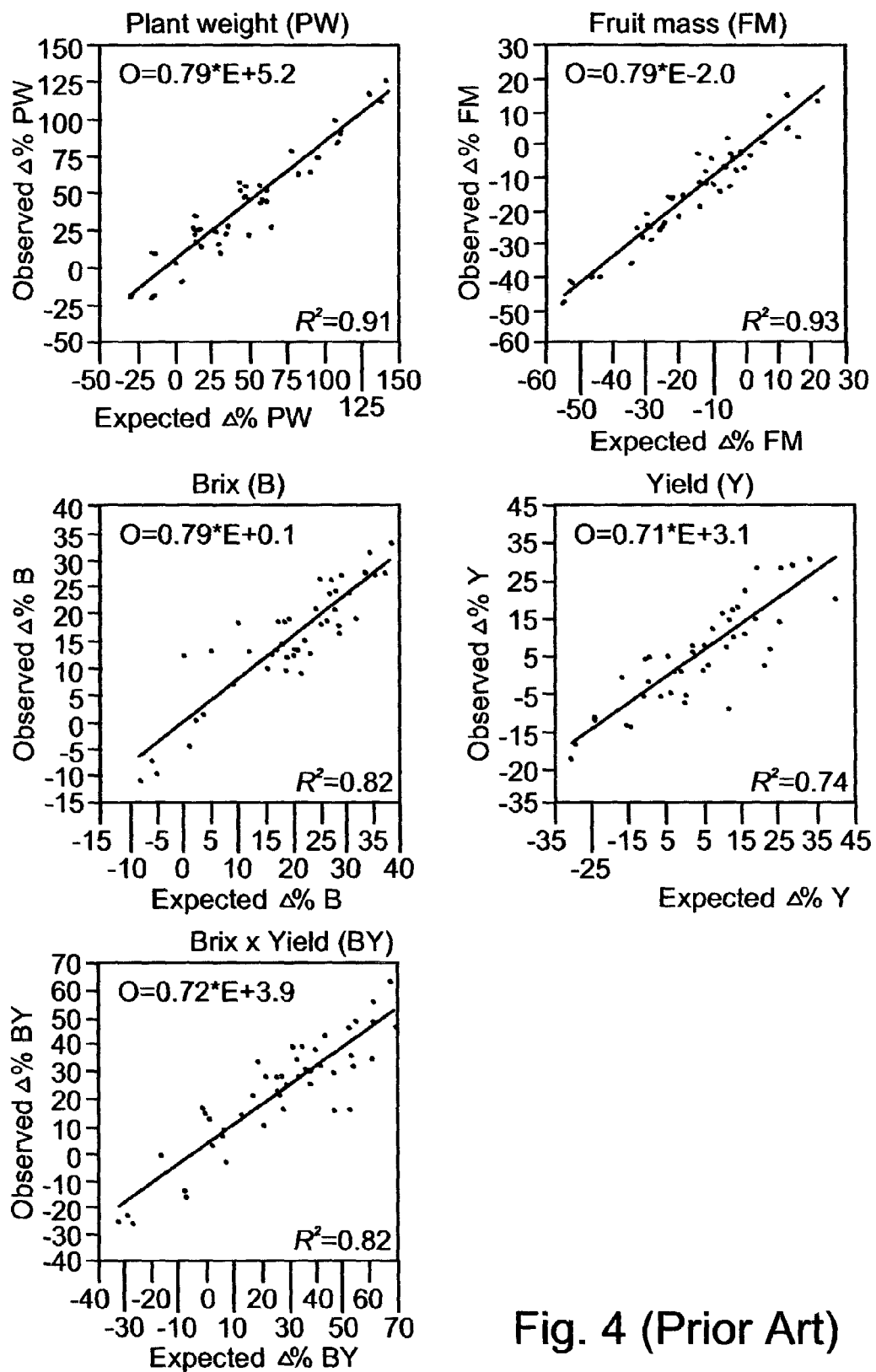
FIG. 4 depicts the relationship between the expected an observed values for plant weight, fruit mass, brix, yield, and brix x yield of 45 hybrids of two ILs. Expected values were calculated on the basis of complete additivity of the effects of the individual ILHs. (prior art).

To search for general trends in the interaction of QTLs, the observed values of the 45 double-heterozygous hybrids were plotted against their expected values (FIG. 4).

For all five traits highly significant linear regressions were found, indicating the overall additivity of the effects of the independent introgressions. Assuming complete additivity between the effects of the combined individual introgressions one would expect a regression with a slope of 1. The slopes of the lines for the five traits were significantly lower than 1 (ranging from 0.71–0.79), indicating average combined effects which are less than additive.

To further examine the less than additive trend revealed by the regression analysis, only the cases of epistasis between significant QTL affecting the traits in the same direction were examined irrespective of whether the QTL originated from *L. pennellii* or *L. esculentum*.

Twenty-nine epistatic interactions between *L. pennellii* introgressions were detected. In all cases, the observed means for the double heterozygous ILHs were significantly lower than the values expected on the basis of an assumption of complete additivity. Seven of the interactions of QTL affecting the trait in the same direction involved *L. pennellii* introgressions with *L. esculentum* alleles. In these cases (row 2 of Table 3), the *L. pennellii* introgressions affected the trait in an opposite manner to that expected according to the parental phenotype (transgressive QTL). Six of the seven interactions were less than additive; the only exception was PW for the hybrid of IL1-1×IL2-1. In this case the double heterozygous hybrid for the QTL acting in the same direction (ILH1-1) showed a higher mean value than the sum of the two independent QTL (M82 and IL2-1×IL1-1). Overall, 35 of the 36 interactions (97%) showed less than additive interactions.

Figure 5:
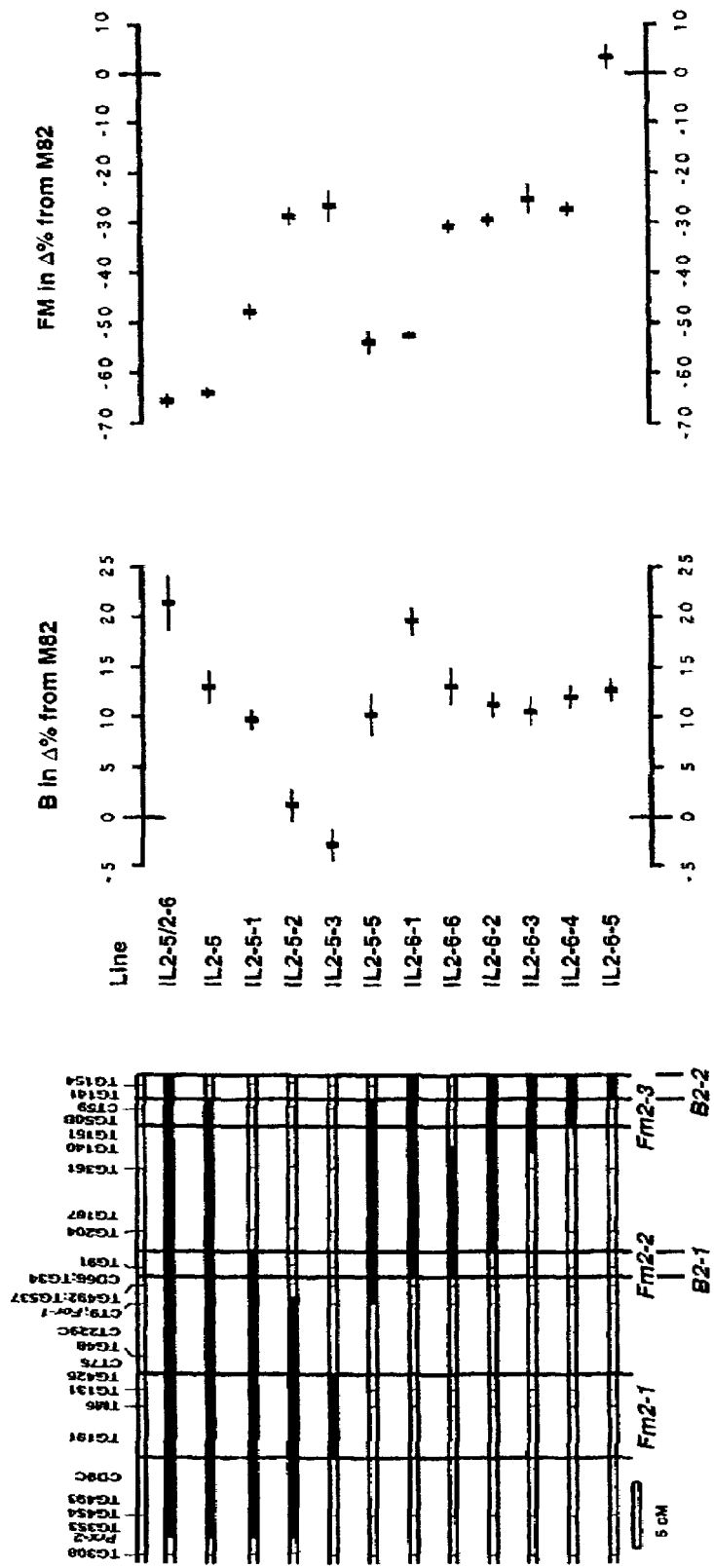
FIG. 5 depicts the fine mapping of linked QTLs for B and FM on the long arm of chromosome 2. The dark bars represent the L. pennellii chromosome segments introgressed into M82. Each point is the mean of the estimated introgression effect; bars represent the standard errors of the means. The mean phenotypic value of each line was determined as described in example 2 of the Examples section that follows (prior art).
Figure 6:
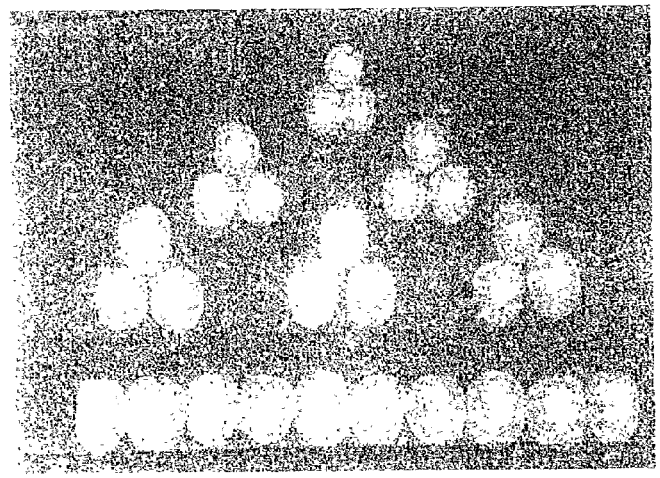
FIG. 6 is a photograph depicting the fruit size of lines used for the mapping analysis of the linked QTL on chromosome 2. Top, IL2-5. Second row: left, IL2-5-1; right, IL2-6-1. Third row: left, IL2-5-3; center, IL2-6-6; right, IL2-6-4. Bottom, M82 (prior art).

Interactions Between Linked QTL (Chromosome 2):

Twelve homozygous ILs with different introgression sizes in chromosome 2 were evaluated for FM and B. Since 10 of these lines were previously tested (Eshed and Zamir 1995, ibid) and no significant interactions between year and IL were detected, the results from the two years were pooled. Based on the overlapping recombined chromosome segments and the phenotypic value of each of the ILs, two B QTL and three FM QTL, responsible for a similar reduction in fruit mass, were mapped (FIGS. 5–6). After determining the positions of these QTL, the lines were classified according to their postulated genotypes (Table 4).

TABLE 4

Interactions of linked QTLs responsible for brix and fruit mass

| Genotypic group[a] | Mean brix (B) in Brix units | Mean brix Δ % from M82 | P value of interaction |
|---|---|---|---|
| No QTL[b] | 4.47 | −0.2 | |
| B2-1 | 5.00 | 11.7 | |
| B2-2 | 4.98 | 11.6 | |
| B2-1/2-2 | 5.37 | 19.9 | 0.03 |

| Genotypic group[a] | Mean Fruit mass (FM) in grams | Mean FM Δ % from M82 | P value of interaction |
|---|---|---|---|
| No QTL[b] | 59.5 | 0.6 | |
| Fm2-1 | 43.0 | −27.3 | |
| Fm2-2 | 41.0 | −30.7 | |
| Fm2-3 | 42.7 | −27.8 | |
| Fm2-1/2-2 | 30.7 | −48.2 | 0.009 |
| Fm2-2-/2-3 | 28.0 | −52.7 | 0.03 |
| Fm2-1/2-2/2-3 | 21.0 | −64.6 | <0.0001/ <0.0001[c] |

[a]genotypic groups were pooled on the basis of the fine mapping analysis presented in FIG. 5.
[b]M82 was included in this group, which includes lines without an L. pennellii QTL which affects this trait.
[c]The two tested interactions were Fm2-1 × Fm2-2/2-3 and Fm2-3 × Fm2-1/2-2

Epistasis for B and FM was tested by comparing the means of the pooled genotypic groups. The single interaction for B was significant and the sum of the effects of the single QTL was higher than the mean value of the lines carrying both QTL. The four different tests for FM QTL interactions were significant: two of them examined the combined action of a single QTL and two examined a single QTL and the remaining pair. The average diminishing effect for two QTL was 8.5% compared to 16.2% for interactions involving the three QTL (Table 3). This result suggests that the effect of the less than additive epistasis is increased (i.e. the effects are further diminished) when more QTL are involved.

The nearly isogenic nature of the IL population utilized by this study allows the identification of twice as many QTL affecting FM and B as in other interspecific studies in tomato (Eshed and Zamir, 1995, ibid). The isogenic nature of the IL population is also responsible for the ability to determine epistasis of QTL through the design of experiments with balanced representation of the different genotypes. Nearly isogenic lines were previously demonstrated to be very efficient for the detection of epistasis of QTL in *Drosophila* (Long et al. 1995, Genetics 139:1273–1291) and maize (Doebley et al. 1995, Genetics 141: 333–346). In conventional segregating populations (F2/F3, BC and recombinant inbreds) all the QTLs which affect the trait are segregating QTLs. Assuming that the less than additive mode of epistasis detected in this study is common to other tomato crosses, this interaction would reduce the effect of individual QTLs. As a consequence, the number of significant QTLs would be underestimated. Less than additive interactions among QTL ensure that the "loss" of an allele affecting a fitness trait will have a minimal effect on the phenotype and that canalization will be achieved.

Contrary to past QTL mapping studies that uncovered little evidence for epistasis, QTL epistasis is an important component in determining the phenotypic value for traits showing continuous variation (Table 3). Of the 93 combinations of pairs of significant QTLs, 39% were epistatic at a significance level of $p<0.05$. Moreover, a higher frequency of epistasis than expected by chance alone was detected for *L. pennellii* chromosome segments that individually did not affect the traits (17%).

Thus, the prevalence of epistasis uncovered by this study is consistent with the numerous classical studies of quantitative traits and breeding that show significant overall epistatic effects for quantitative traits detected through biometrical genetics.

Example 3

Separating the Positive Trait for High Brix Value from the Negative Traits of Percentage Green Fruit Yield and Internodes Length Through Marker Assisted Selection As is described in Examples 1 and 2, the hybrid plants obtained from introgressing *L. pennellii* into a *L. esculentum* genetic background detected numerous QTLs associated with traits such as brix (B) and fruit mass (FM). However, these studies failed to isolate the QTL associated with brix from other QTLs which are associated with negative traits such as high percentage of green fruit yield and long internodes.

As such, while reducing the present invention to practice a hybrid plant (IL9-2-5) resultant from these studies was further introgressed into the genetic background of an *L. esculentum* cultivated tomato variety (M82) in efforts to isolate the QTL associated with brix from other QTLs responsible for these negative traits which are present in IL9-2-5, to thereby obtain a plant line bearing fruits characterized by a high sugar content (high brix value) while being otherwise similar in phenotype to a cultivated tomato.

Figure 7:
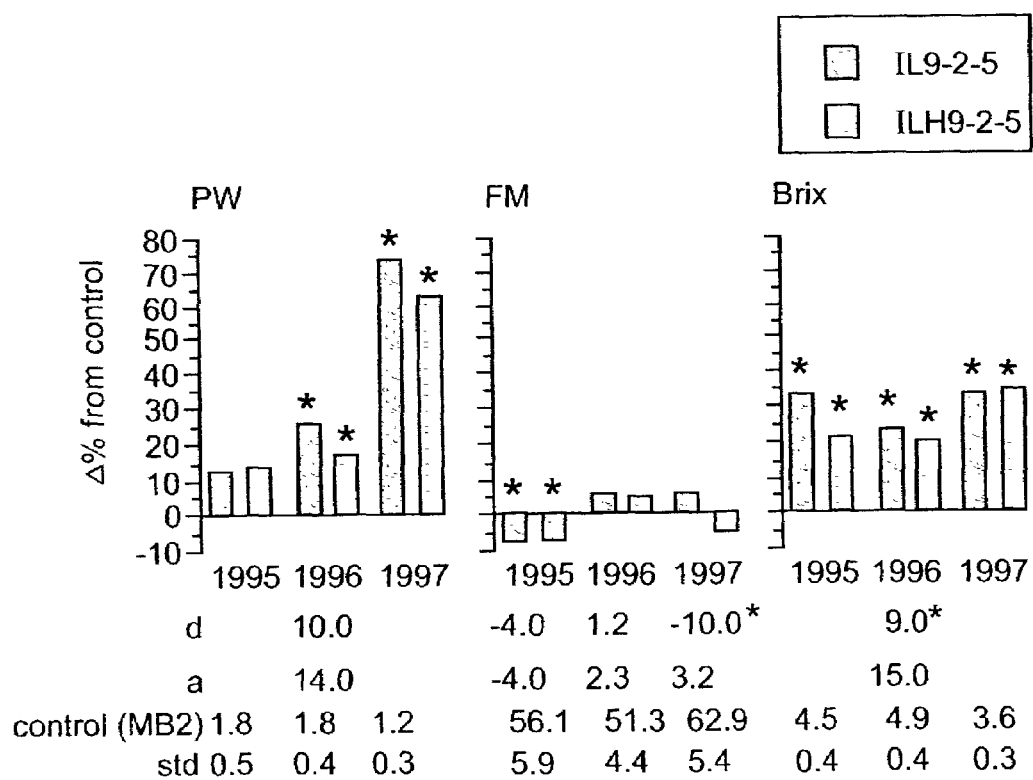
FIG. 7 depicts an interaction between IL9-2-5 and the year grown as expressed by plant weight (PW), fruit mass (FM) and brix (B). The values of IL9-2-5 and the hybrid ILH9-2-5 over the years 1995, 1996 and 1997 are expressed as the percent difference from the isogenic control M82 ($\Delta\%$ of M82). Results for IL9-2-5 are indicated by the gray bars while results for ILH9-2-5 are indicated by the ladder bars. * above the bars denotes a significance difference ($p<0.01$) from the control and * in the d values represents a significant ($p<0.05$) dominance deviation of the heterozygous. For the traits showing no yearly dependence (alpha level=0.01) data from the three years was pooled to estimate a and d. The mean and the standard deviation values for M82 are indicated at the bottom of the Figure; PW- Kg, FM-g; B-%.

To estimate the phenotypic variation associated with high brix value, near isogenic plants derived from self crossing of M82 and IL9-2-5 and hybrids generated from crossing M82 and IL9-2-5, were evaluated over a three year period. FIG. 7 presents the means of the tested genotypes for total soluble-solids (brix, B), plant weight (PW) and fruit mass (FM).

The 9-2-5 (chromosome 9) introgression was responsible for a significant reduction (10%) in FM in 1995 while in the following years its effects were not significant. The effect of the introgression on B was consistent between the different years; the introgression significantly increased B from 20 to 32 percent relative to the control showing partial dominance (d/a=0.64). In 1995, the introgression increased PW by ten percent compared to 70 percent in 1997; yet, the effect of the introgression on B was similar in these two years, indicating that PW is not involved in the major pathway affecting B. Hybrid high brix value plants that carried the introgression were more vegetative, with longer internodes and the ripening of the fruit lasted a longer period (late variety) and as such are of little commercial value.

In order to generate hybrids characterized by a uniform and early ripening, a good cover of the fruit and a high brix value, which hybrids are of high commercial value, it was decided that further narrowing of the 9-2-5 introgression chromosomal region (9 cM) must be effected in order to isolate the brix QTL.

Figure 8B:
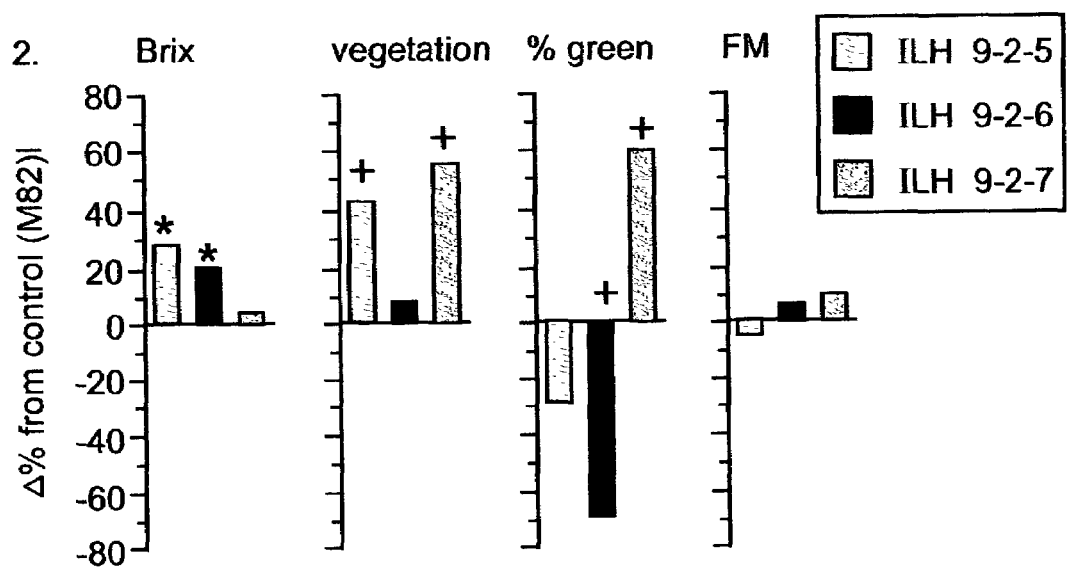
FIG. 8*b* depicts the phenotypic effects of the IL9-2-5 (ladder bar), IL9-2-6 (black) and IL9-2-7 (white) hybrids compared to the control M82. * and + above the bars denote a significance difference (p<0.05, p<0.1, respectively) from the control. Each value represents the mean of eight plots.

In order to verify if the increase in brix and the negative effects described above which are associated with the 9-2-5 introgression are due to linkage drag or are simply pleiotropic effects of the QTL, sub-lines of IL9-2-5 (IL9-2-6 and IL9-2-7) were generated by selfing the IL9-2-5 hybrid and screening for recombinants in the introgression. IL9-2-6 and IL9-2-7 carried the south (in direction of the centromere) and north (in direction of a telomere) part of the introgression, respectively (FIG. 8a). Plants of M82 and hybrids generated from crossing M82 with the IL9-2-5, IL9-2-6 and IL9-2-7 plant lines (termed ILH9-2-5, ILH9-2-6 and ILH9-2-7, respectively) were planted in a commercial stand and evaluated for B, FM, vegetation and % of green fruit yield as a parameter for the uniformity of the ripening. FIG. 8b presents the mean effects of the tested hybrids as is compared to the control tomato plant M82. The short introgressions of IL9-2-7 showed the "negative" phenotype of IL9-2-5 with high vegetation, longer internodes and late maturity, but had no significant effect on B. IL9-2-6 had a significant increasing effect on B with a reduced vegetation and an early and uniform ripening. The three hybrids had no significant effects on the FM.

Thus, these results place the brix QTL in the south part of the 9-2-5 introgression (FIGS. 8a and 10bw). A hybrid plant (ILH9-2-6) generated from introgressing IL9-2-6 in the M82 genetic background is characterized by fruit having an increased sugar content (B) similar to that of the IL9-2-5 hybrid plant line, without the undesired traits found in IL9-2-5 which are generated by genes situated in the northern part of the 9-2-5 introgression (9-2-7).

Example 4

The study described in Example 3 which was conducted as part of the present invention and previously published studies described in Examples 1 and 2, were performed in a genetic background of determinate tomato lines that were specifically developed for the processing tomato industry (M82). These plants are suitable for "once over" machine harvest due to homozygosity for the recessive mutation sp (self pruning) which modifies the developmental program of the shoot such that growth is terminated after the production of two consecutive inflorescences.

The wild species (green-fruited) and greenhouse cultivated tomatoes are indeterminate ($S^p$+) where the shoot follows a uniform developmental program of three leaves and an inflorescence throughout the growth (Pnueli et al. 1998, Development 125:1979–1989). Indeterminate greenhouse tomatoes require different agricultural practices as is compared to determinate varieties and therefore constitute a fundamentally different genetic background to test the effect of the brix QTL.

Figures 9, 10A:
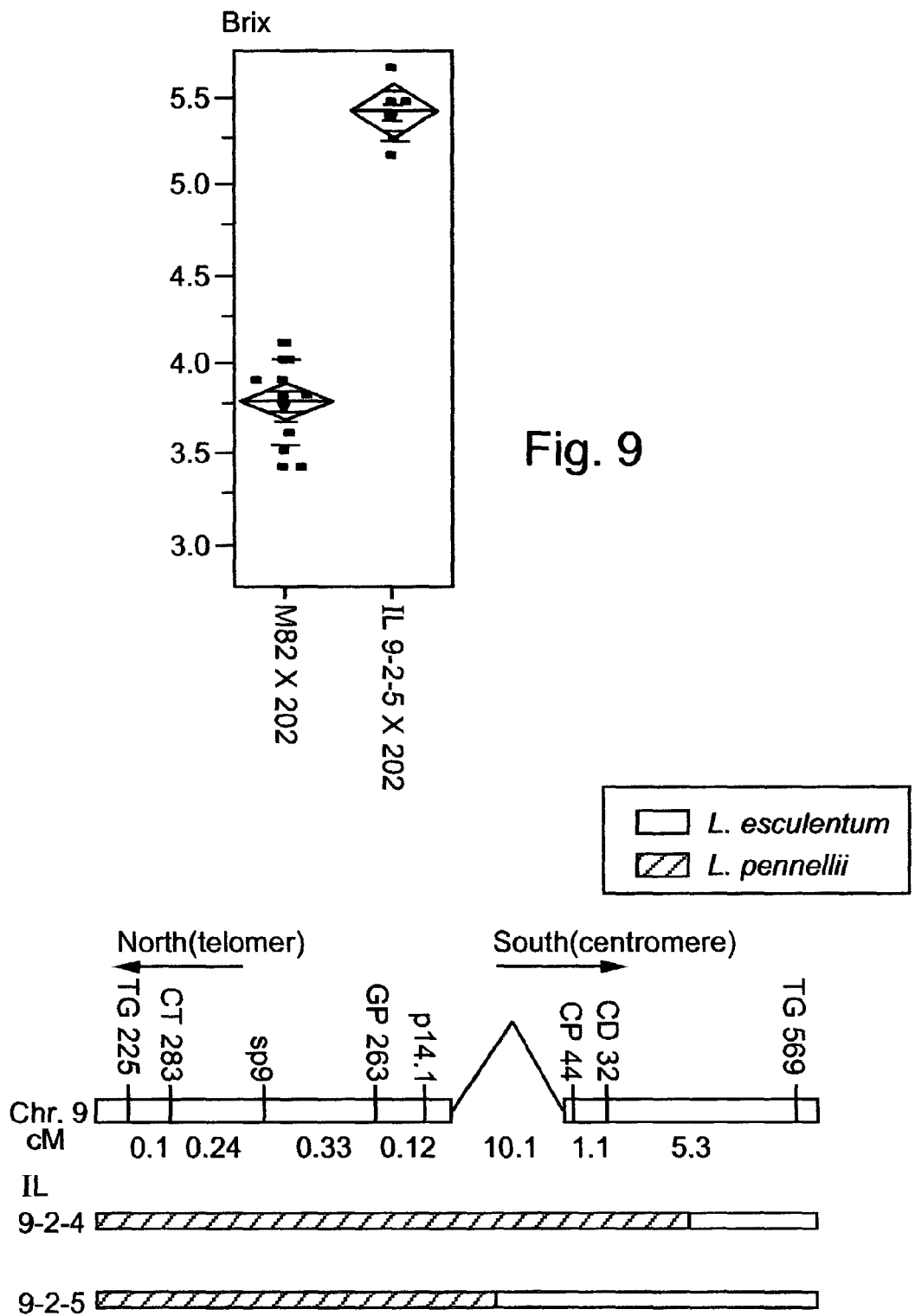
FIG. 9 is a scatter plot depicting brix values of two isogenic hybrids, M82×line 202 (17 plants) and IL9-2-5× line 202 (8 plants). The center lines of the means (diamonds) are the group means. The top and bottom of the diamonds form the 95% confidence intervals for the means.
FIGS. 10*a–b* illustrate the IL9-2-5 and IL-9-2-4 introgressions with respect to tomato chromosome 9.

M82 and IL9-2-5 were crossed with an indeterminate greenhouse line (202) and the two nearly isogenic indeterminate hybrids were grown in the greenhouse and evaluated for B. The introgression was responsible for a 40 percent increase in B with a separation of the values into discrete groups (FIG. 9). This result gave a motivation to develop NILs for the chromosome 9 introgression in the genetic background of line 202.

Figure 11:
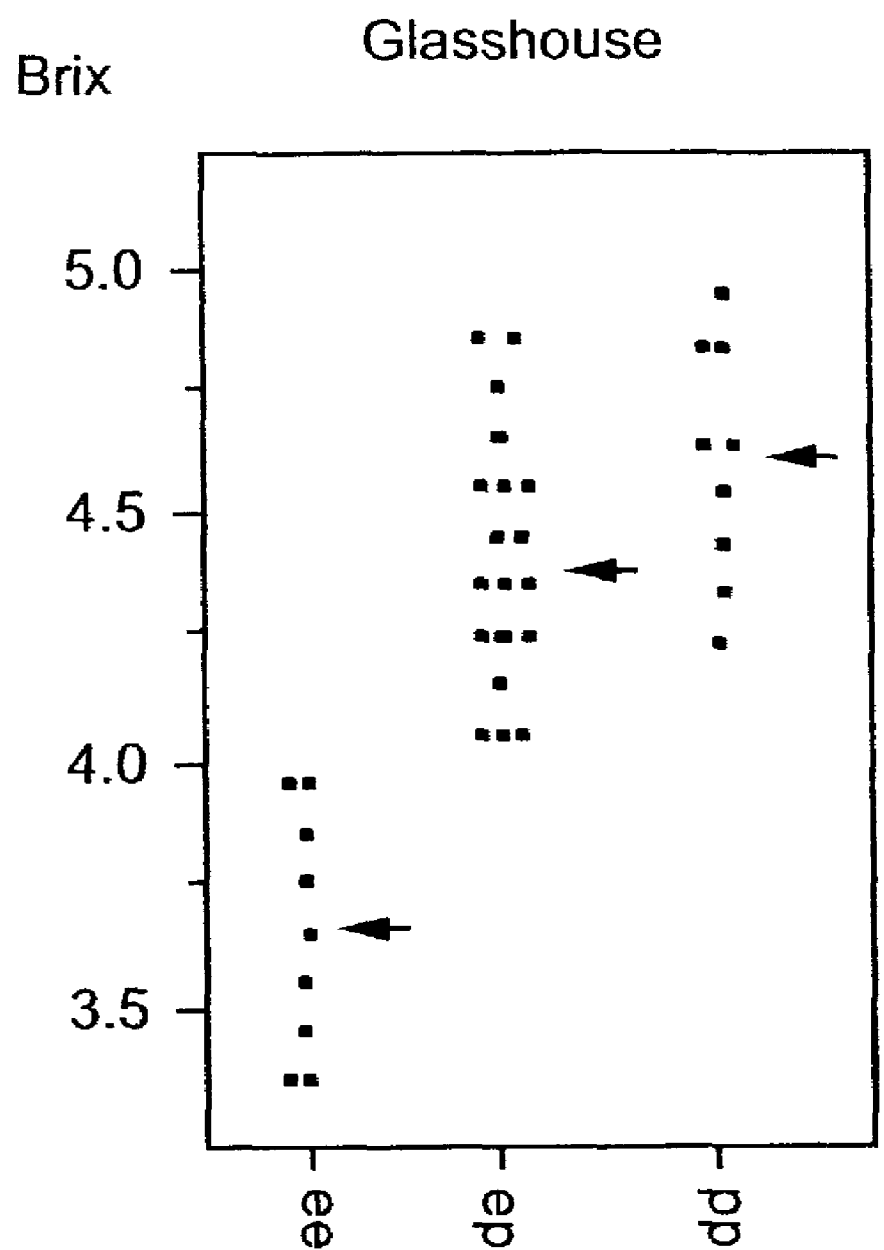
FIG. 11 is a collection of scatter plots depicting the effects of brix 9-2-5 in the 3-year trial of the indeterminate (glasshouse) NILs. e—*L. esculentum*, p —*L. pennellii*. The homozygous IL (pp), containing segment of chromosome 9, improved B by 27 percent over the control (ee) with partial dominance for the wild species segment (ep) (a=0.5, d=0.25, d/a=0.5). Black arrows and horizontal gray lines mark the mean values and the 99.9% confidence interval for each genotype.

The initial material for the introduction of the brix QTL into indeterminate background was the IL9-2-4 introgression line (FIGS. 10a–b). This introgression extends to the south of the chromosome beyond the 9-2-5 introgression. This line was selected since it was observed that recombinants are more efficiently obtained when long introgressions are used in the marker assisted selection. After five marker-assisted backcrosses the selfed generation of a BC5 plant that was heterozygous for the introgression was grown and the segregating population was subjected to RFLP analysis. The results were highly consistent between the determinate and indeterminate backgrounds (FIG. 11); the homozygous IL, containing segment of chromosome 9, improved B by 27% over the control with partial dominance for the wild species segment (a=0.5, d=0.25, d/a=0.5). Very similar results were obtained in another growing season (data not presented) confirming that the observed effects were independent of environment in the greenhouse.

Thus, a major brix associated QTL was introgressed into a genetic background of an indeterminate greenhouse tomato (202) thus yielding plants which are high in brix and which in all other aspects are similar in phenotype to this indeterminant greenhouse tomato line. In addition, the resultant tomato line does not display the undesirable self pruning trait inherent to determinate tomato lines specifically developed for the processing tomato industry (M82).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Deposit Information

A deposit of the De Ruiter Seeds R&D B.V. proprietary tomato line *L. pennellii* IL 9-2-6 disclosed above and recited in the appended claims has been made with NCIMB Ltd., Ferguson Building, Craibstone Estate, Bucksburn, Aberdeen, AB21 9YA, Scotland, an International Depository Authority under the Budapest Treaty. The dates of deposit were Mar. 2, 2006 and Oct. 2, 2006. The deposit of seeds is a representative sample of material that was in existence prior to the filing date of this application. All restrictions upon the deposit will be removed upon granting of the patent, and the deposit is intended to meet all of the requirements of 37 C.F.R. §§801–1809. The NCIMB I.D. number is NCIMB 41379 and the identification reference name is *Solanum lycopersicum* BRIX IL 9-2-6. The deposit will be maintained in the depository for a period of 30 years, or 5 years after the last request, or for the effective life of the patent, whichever is longer, and will be replaced as necessary during that period.

What is claimed is:

1. A cultivated tomato plant of the species *Lycopersicon esculentum* having a genome comprising an introgression derived from *Lycopersicon pennellii*, said introgression increasing the Brix value of fruits of said cultivated tomato plant by at least 6% as compared to a plant of the same genotype without the introgression, where said introgression consists essentially of the introgression of tomato plant *Lycopersicon pennellii* IL 9-2-6.

2. The cultivated tomato plant of claim 1, wherein fruits of the cultivated tomato plant are characterized by an average fruit mass greater than 30 grams.

3. The cultivated tomato plant of claim 1, wherein internodes of the cultivated tomato plant are shorter than 15 cm.

4. The cultivated tomato plant of claim 1, wherein the cultivated tomato is of a determinate or semideterminate tomato line.

5. The cultivated tomato plant of claim 1, wherein said cultivated tomato is of an indeterminate tomato line.

6. A tomato fruit of the tomato plant of claim 1.

7. A method of generating a cultivated *Lycopersicon esculentum* tomato plant having fruits characterized by an increased Brix value, the method comprising the step of introgressing to a genome of said tomato plant an introgression from *Lycopersicon pennellii*, said introgression increasing the Brix value of fruits of said cultivated tomato plant by at least 6% as compared to a plant of the same genotype without the introgression, where said introgression consists essentially of the introgression of tomato plant *Lycopersicon pennellii* IL 9-2-6.

8. The method of claim 7, wherein said fruits of the cultivated tomato plant are characterized by an average fruit mass greater than 30 grams.

9. The method of claim 7, wherein internodes of the cultivated tomato plant are shorter than 15 cm.

10. The method of claim 7, wherein the cultivated tomato is of a determinate or semideterminate tomato line.

11. The method of claim 7, wherein said cultivated tomato is of an indeterminant indeterminate greenhouse tomato line.

12. A tomato fruit derived from the method of claim 7.

13. A method of generating a tomato plant having fruits characterized by an increased Brix value, the method comprising the steps of:
  (a) crossing a first cultivated *Lycopersicon esculentum* tomato with tomato line *Lycopersicon pennellii* IL 9-2-6, so as to generate a first hybrid tomato characterized by a fruit Brix value higher than that of said cultivated *Lycopersicon esculentum* tomato;
  (b) crossing said first hybrid tomato or offsprings thereof with a second cultivated *Lycopersicon esculentum* tomato being characterized by a phenotype different than said first cultivated *Lycopersicon esculentum* tomato; and
  (c) isolating offsprings resulting from step (b) characterized by a phenotype of said second cultivated *Lycopersicon esculentum* tomato yet with fruits having a higher Brix value than that of fruits of said second cultivated *Lycopersicon esculentum* tomato.

14. The method of claim 13, further comprising the step of:
  (d) selfing said offsprings resultant from step (c) so as to establish a tomato line characterized by a phenotype of said second cultivated *Lycopersicon esculentum* tomato yet with fruits having said higher Brix value than that of fruits of said second cultivated *Lycopersicon esculentum* tomato.

15. A seed of the tomato plant of claim 1.

16. A method of producing a hybrid, selfed or backcrossed plant, the method comprising the step of crossing the cultivated tomato plant of claim 1 with a cultivated *Lycopersicon esculentum* tomato plant.

17. A method of producing a tomato seed of the plant of claim 16, comprising the step of crossing the cultivated tomato plant of claim 1 with a cultivated *Lycopersicon esculentum* tomato plant and deriving a tomato fruit that has produced said tomato seed.

18. A tomato seed designated *L. pennellii* IL 9-2-6, a sample of said seed having been deposited under National Collection of Industrial Bacteria number NCIMB 41379.

19. A tomato seed including a genome comprising an introgression derived from *Lycopersicon pennellii*, said introgression increasing the Brix value of fruits from a tomato plant grown from said tomato seed by at least 6% as compared to a plant of the same genotype without the introgression, where said introgression consists essentially of the introgression of tomato plant *Lycopersicon pennellii* IL 9-2-6.

20. A tomato plant, or parts thereof produced by growing the seed of claim 19.

21. Pollen of the plant of claim 1.

22. A tomato seed produced by growing said tomato plant of claim 20, wherein the genome of said tomato seed comprises said introgression.

23. A tomato plant, or parts thereof, produced from seed of claim 22.

* * * * *

SEQUENCE LISTING

<160> NUMBER OF SEQ ID NOS: 1

<210> SEQ ID NO 1
<211> LENGTH: 500
<212> TYPE: DNA
<213> ORGANISM: Lycopersicon esculentum

<400> SEQUENCE: 1

```
ttctgcaaga agataaaata atataatttt ttctagtaat ttaaatatta tatgtgaata      60
ttgtaagtta aacatgaagt tcacaaggag agtatatgat tatatgatta attaaagatt     120
tagacaaaat taaagggtat ttttggtacg acgtaaaaat aactttttag aaaatatttt     180
tgcgagtata ttatttatta atgttttata ctaatataga agtcgttatt tttagggaaa     240
```

-continued

```
aaaagttctt ttcaaaatat gaaataaatt tctagcctag ggacgaaagt ctttttttttt    300 tttataacta tagtaaacgt aaaatcacgt aattaaaaca tttataataa taaaagataa    360
aagatctata ttggttttac caattagtac atattaggtt ttagtcacgt taatatgttt    420 actttttttgt tctaatatta gtaattatct attaatcttg taatagctaa tttttttatt    480
ttttttttgt aattgattaa                                                 500
```